US012102455B2

(12) United States Patent
Lund et al.

(10) Patent No.: US 12,102,455 B2
(45) Date of Patent: *Oct. 1, 2024

(54) SYSTEMS, MONITOR MOUNTS AND MONITORS

(71) Applicant: Drägerwerk AG & Co. KGaA, Lübeck (DE)

(72) Inventors: Peter A. Lund, Nashua, NH (US); Thomas Swyst, Arlington, MA (US); Christopher Aiston, Mont Vernon, NH (US); Zachary K. Hennings, Reading, MA (US)

(73) Assignee: Drägerwerk AG & Co. KGaA (DE)

( * ) Notice: Subject to any disclaimer, the term of this patent is extended or adjusted under 35 U.S.C. 154(b) by 575 days.

This patent is subject to a terminal disclaimer.

(21) Appl. No.: 17/419,137

(22) PCT Filed: Jul. 2, 2019

(86) PCT No.: PCT/EP2019/067781
§ 371 (c)(1),
(2) Date: Jun. 28, 2021

(87) PCT Pub. No.: WO2020/135935
PCT Pub. Date: Jul. 2, 2020

(65) Prior Publication Data
US 2022/0104779 A1 Apr. 7, 2022

Related U.S. Application Data

(60) Provisional application No. 62/786,047, filed on Dec. 28, 2018.

(51) Int. Cl.
*A61B 5/00* (2006.01)
*H05K 5/00* (2006.01)
*H05K 5/02* (2006.01)

(52) U.S. Cl.
CPC ......... *A61B 5/7445* (2013.01); *H05K 5/0017* (2013.01); *H05K 5/0204* (2013.01); *A61B 2560/045* (2013.01)

(58) Field of Classification Search
None
See application file for complete search history.

(56) References Cited

U.S. PATENT DOCUMENTS 9,131,904 B2 * 9/2015 Qualey .................. A61B 5/002
9,153,112 B1 10/2015 Kiani et al.
9,168,006 B2 * 10/2015 Georgiev ............... A61B 5/021
9,436,645 B2 * 9/2016 Al-Ali ................ A61B 5/02055
(Continued)

FOREIGN PATENT DOCUMENTS

WO 2018125572 A1 7/2018

OTHER PUBLICATIONS

European Patent Office, The International Search Report and The Written Opinion of the International Searching Authority, Oct. 14, 2019, for International Application No. PCT/EP2019/067781.

Primary Examiner — Xanthia C Relford
(74) Attorney, Agent, or Firm — Design IP

(57) ABSTRACT

A monitor mount is configured to detachably secure a first monitor and/or a second monitor individually or concurrently. The first monitor and the second monitor may have different sizes. Any of the monitors may be a patient monitor.

24 Claims, 18 Drawing Sheets

(56) References Cited

U.S. PATENT DOCUMENTS

| | | | |
|---|---|---|---|
| 9,439,574 B2* | 9/2016 | McCombie | G16H 40/63 |
| 10,918,281 B2* | 2/2021 | Al-Ali | A61B 5/0022 |
| 11,605,188 B2* | 3/2023 | Al-Ali | G06T 11/206 |
| 2012/0194327 A1* | 8/2012 | Schuman, Sr. | G08B 25/00 |
| | | | 340/286.07 |
| 2014/0159921 A1* | 6/2014 | Qualey | H05K 7/00 |
| | | | 361/679.01 |
| 2018/0130325 A1* | 5/2018 | Kiani | A61B 5/08 |
| 2018/0242926 A1* | 8/2018 | Muhsin | G16H 40/67 |
| 2018/0256111 A1* | 9/2018 | Ganapathy | G16H 50/30 |
| 2019/0069778 A1* | 3/2019 | Pourhoseini | A61B 5/0022 |
| 2019/0183435 A1* | 6/2019 | Eslava | G16H 40/63 |

* cited by examiner

SYSTEMS, MONITOR MOUNTS AND MONITORS

FIELD OF THE DISCLOSURE

The present disclosure generally relates to: a monitor mount that is able to receive differently sized monitors, and more specifically, to a monitor mount that enables data transfer between the monitor mount and the monitors received thereby; a first monitor that is able to interface with a second monitor and the monitor mount; and systems comprising any one or more of the above.

BACKGROUND OF THE DISCLOSURE

Monitors that include electronic visual displays are utilized in a large number of applications within a wide variety of industries including, for example, the healthcare industry, the military, and the oil and gas industry. Many of the applications within such industries require such monitors to, at times, be portable, and, at other times, be stationary. For example, in the healthcare industry, when not being used in transport of a patient or when a patient is ambulatory, monitors can be connected to a monitor mount. Such monitor mounts can provide a variety of functions including providing physical support, a power source, and a conduit to one or more computer networks.

One type of monitor is a patient monitor which is used by healthcare facilities to monitor and display information about a patient, such as vital signs, status of connected devices (e.g., physiological sensors, etc.), and the like. Patient monitors can be portable devices that travel with the patient in order to provide continuous monitoring during care. When a patient arrives at a hospital room or other treatment location, the patient monitor is often plugged into or otherwise connected to a patient monitor mount. Patient monitor mounts provide a physical interface for the patient monitor and are generally fixed to the treatment location. Patient monitor mounts can also provide electrical connection to other devices or infrastructure, such as power to recharge patient monitor batteries, network connectivity to other medical devices or hospital computer systems, and the like.

During the course of providing healthcare to patients, practitioners typically connect at least one type of sensor to a patient to sense, derive or otherwise monitor at least one type of patient medical parameter. Such patient connected sensors are further connected to the monitor that includes all relevant electronic components that enable conversion, manipulation and processing of the data sensed by the at least one type of sensor in order to generate patient medical parameters. These patient medical parameters may be stored in one or more modules and are usable by healthcare practitioners (e.g., nurses, doctors, physician assistants, or any other person charged with providing a healthcare service to a patient) in monitoring a patient and determining a course of healthcare to be provided to the patient. Additionally or alternatively, the one or more modules may contain data, such as patient treatment data, to be transferred to the monitor mount and/or the monitor.

The monitor may be selectively connected to a patient at any point during which a healthcare professional comes into contact with the patient and may remain connected with the patient as the patient moves through various locations within a particular healthcare enterprise (e.g., hospital) or between different healthcare enterprises (e.g., an ambulance and/or different medical facilities). The monitor and/or the module can allow data representing the at least one patient medical parameter to be communicated to other systems within the healthcare enterprise. This data may then be used by different systems in further patient care.

Patient monitors have different sizes and provide different functionalities. With current systems, each type of patient monitor typically requires a dedicated monitor mount, a dedicated controller, and a dedicated user interface. Accordingly, such monitors are not interoperable and the performance advantages of each type of monitor cannot be combined and leveraged.

In addition, there is a growing need in acute care environments to improve clinical workflow, reduce alarm fatigue, and customize medical devices to better suit hospital protocols and use models.

Due to the above problems associated with current systems, there is a need for a modular system providing a universal and scalable platform including a monitor mount capable of mixed use with monitors having different sizes which are interoperable with the same controller and the same user interface, and that can be universally docked to the monitor mount.

SUMMARY OF THE DISCLOSURE

In light of the above, the present disclosure is broadly directed to a system comprising a monitor mount, a first monitor and a second monitor. The monitor mount includes a first coupling and a support portion, the first monitor includes a first electronic visual display and a first back portion, and the second monitor includes a second electronic visual display, a second back portion and a second coupling. The first monitor is configured to be detachably secured to the monitor mount by the first coupling. The second monitor is configured to be detachably secured to the monitor mount by the first coupling and the support portion. Each of the first back portion of the first monitor and the second back portion of the second monitor is configured to be detachably secured to the monitor mount by the first coupling. The first monitor is configured to be detachably secured to the second monitor by the second coupling. The second monitor is configured to surround at least a portion of the first electronic visual display of the first monitor when the first monitor is detachably secured to the second monitor. The second monitor can surround only a portion of the first monitor such that ends of the first monitor in a lateral direction of the first monitor are exposed. The monitor mount is able to secure each of the first monitor and the second monitor individually or both of the first monitor and the second monitor concurrently. In other words, the first coupling is configured to accept either the first monitor or the second monitor such that the monitor mount is configured to mount the first monitor alone, the second monitor alone, or a combination of the first monitor and the second monitor.

The monitor mount can also include a first power bus. The first monitor and/or the second monitor can optionally be powered by the first power bus when secured to the monitor mount.

The first monitor and/or the second monitor can also include a second power bus. If only one of the first monitor and the second monitor includes a second power bus, the other of the first monitor or the second monitor can be powered by the second power bus when the first monitor is secured to the second monitor. The first monitor and/or the second monitor, in some variations, is operable solely via the second power bus. In other variations, the first monitor and/or the second monitor is operable via either of the first power bus and the second power bus.

The first monitor and/or the second monitor can include a self-contained power source that allows the first monitor and/or the second monitor to be operated independently of the monitor mount.

The first monitor can include a sensor interface configured to receive data generated by at least one physiological sensor monitoring a physiological parameter of a patient. The at least one physiological sensor can include a wired connection to the sensor interface. The at least one physiological sensor can additionally or alternatively include a wireless connection to the sensor interface.

The second monitor can be a multiparameter monitor for continuously monitoring adult, pediatric and neonatal patients both at a bedside and on transport and can support all patient acuity levels hospital-wide.

Either of the first monitor or the second monitor can capture and display real-time vital signs at the bedside. Either of the first monitor or the second monitor can be used as a standalone monitor or in combination. The system of the present disclosure integrates patient data and provides continuous monitoring at the bedside and on transport.

The second monitor can be configured to be first coupled to the first coupling and the support portion and the first monitor can be configured to be subsequently coupled to the second coupling.

The first monitor can be configured to be coupled to and power the second monitor by the second power bus of the first monitor when neither of the first monitor and the second monitor are secured to the monitor mount.

The second monitor can be configured to be coupled to and power the first monitor by the second power bus of the second monitor when neither of the first monitor and the second monitor are secured to the monitor mount.

Each of the first coupling and the second coupling can take various forms including a mechanical coupling, an electro-mechanical coupling, and/or a magnetic coupling.

The monitor mount can further include a first communications interface coupled to at least one computing network. With this variation, the first monitor and/or the second monitor can include a second communications interface which transmits and receives data over the computing network via the first communications interface when the first monitor and/or the second monitor is secured to the monitor mount.

The monitor mount can also be configured to detachably secure one or more modules for monitoring the physiological parameter of the patient.

The monitor mount can be mounted at the bedside, from the ceiling, on a wall across the room, or even outside the room for isolation purposes.

The first monitor can visualize at least a portion of received data on the first electronic visual display. The second monitor can visualize at least a portion of received data on the second electronic visual display.

The first monitor can be configured to be detachably secured to and removed from a forward face of the monitor mount. In addition or in the alternative, the first monitor can be configured to be transversely inserted into and removed from the monitor mount. Furthermore, the first monitor can be configured to be transversely inserted into and removed from the monitor mount from each of a first lateral direction of the monitor mount and a second lateral direction of the monitor mount, wherein the first lateral direction of the monitor mount is opposite to the second lateral direction of the monitor mount. Such transverse insertion and removal can be performed with one hand by a user. In other words, it is not necessary to perform two separate motions to transversely insert or remove the first monitor from the monitor mount.

The first monitor can be configured to be transversely inserted into and removed from the second monitor. Furthermore, the first monitor can be configured to be transversely inserted into and removed from the second monitor from each of a first lateral direction of the second monitor and a second lateral direction of the second monitor, wherein the first lateral direction of the second monitor is opposite to the second lateral direction of the second monitor. Such transverse insertion and removal can be performed with one hand by the user. In other words, it is not necessary to perform two separate motions to transversely insert or remove the first monitor from the second monitor.

The system of the present disclosure therefore allows monitors to be mixed and matched across different care areas and geographies such that workflow is optimized. The system of the present disclosure also requires fewer mounting points than current systems, thereby reducing installation and maintenance costs. Since the monitor mount and one or more monitors are integrated and consolidated, the space required for the system of the present disclosure is minimized. The system of the present disclosure can be used in dry and wet zones and contributes to an enhanced level of hygiene. According to caregiver preference, the system of the present disclosure can be scaled to the patient's needs—from basic monitoring to using the full range of all of the monitors. To support individual workflow, multiple monitors can be used, for example, to support anesthesiologists, perfusionists, and surgeons if a surgical display controller is used.

The system of the present disclosure provides a high acuity care system that improves aesthetics and ergonomics by allowing different caregivers to view the information they need at the same place. The system of the present disclosure can be used as part of a healthcare enterprise solution and can bring comprehensive information to the point of care, while continuously monitoring the patient. For example, the system of the present disclosure can provide access to images, lab results and other clinical data, while displaying real-time vital signs data at the point of care. Furthermore, the performance advantages of differently sized monitors can be combined and leveraged. For example, the portability of a smaller monitor and the increased functionality of a larger monitor can be independently or concurrently capitalized upon.

The subject matter described herein provides many technical advantages. For example, the current subject matter enables the mounting of two monitors having different sizes, shapes, and functionality on a single monitor mount.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The following detailed description references the drawings, wherein.

DETAILED DESCRIPTION

Figure 1:
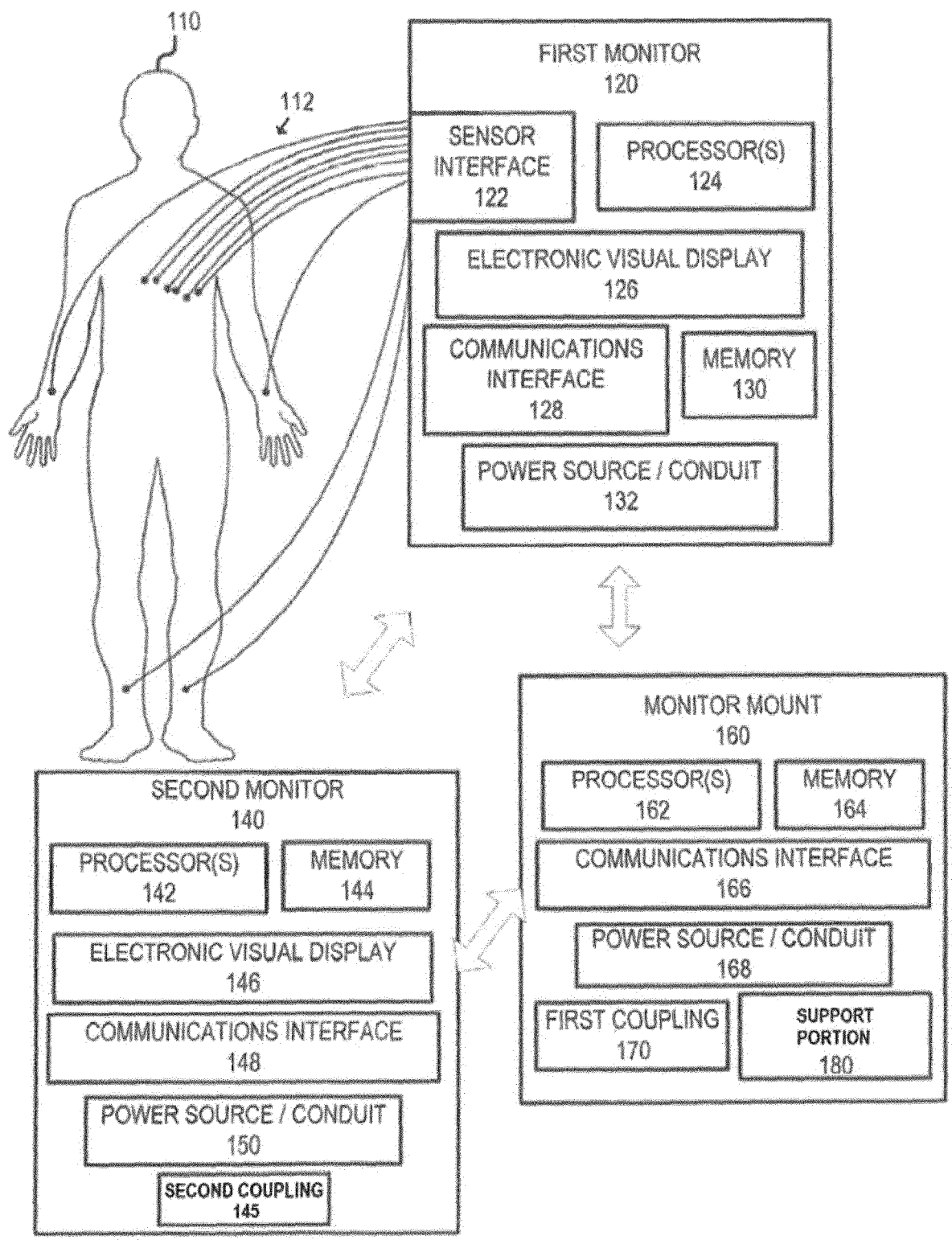
FIG. 1 is a logical diagram illustrating the example system including a first monitor 120, a second monitor 140, and a monitor mount 160.

The following description is made with reference to the accompanying drawings and is provided to assist in a comprehensive understanding of various example embodiments of the present disclosure. The following description includes various details to assist in that understanding, but these are to be regarded as merely examples. Accordingly, those of ordinary skill in the art will recognize that various changes and modifications of the examples described herein can be made without departing from the spirit and scope of the present disclosure. In addition, descriptions of well-known functions and constructions may be omitted for clarity and conciseness.

The terms and words used in the following description and claims are not limited to the bibliographical meanings, but are merely used to enable a clear and consistent understanding of the present disclosure. Accordingly, it should be apparent to those skilled in the art that the following description of the present disclosure is provided for illustration purposes only, and not for the purpose of limiting the present disclosure as defined by the appended claims and their equivalents.

It is to be understood that the singular forms "a", "an", and "the", include plural referents unless the context clearly dictates otherwise. Thus, for example, reference to "a processor" or "a memory" includes reference to one or more of such processors or memories.

The expressions such as "include" and "may include" which may be used in the present disclosure denote the presence of the disclosed functions, operations, and constituent elements, and do not limit the presence of one or more additional functions, operations, and constituent elements. In the present disclosure, terms such as "include" and/or "have", may be construed to denote a certain characteristic, number, operation, constituent element, component or a combination thereof, but should not be construed to exclude the existence of or a possibility of the addition of one or more other characteristics, numbers, operations, constituent elements, components or combinations thereof.

In the present disclosure, the expression "and/or" includes any and all combinations of the associated listed words. For example, the expression "A and/or B" may include A, may include B, or may include both A and B.

In the present disclosure, expressions including ordinal numbers, such as "first", "second", and/or the like, may modify various elements. However, such elements are not limited by the above expressions. For example, the above expressions do not limit the sequence and/or importance of the elements. The above expressions are used merely for the purpose of distinguishing an element from the other elements. For example, a first box and a second box indicate different boxes, although both are boxes. For further example, a first element could be termed a second element, and similarly, a second element could also be termed a first element without departing from the scope of the present disclosure.

Unless otherwise defined, all terms including technical and/or scientific terms used herein have the same meaning as commonly understood by one of ordinary skill in the art to which the present disclosure pertains. In addition, unless otherwise defined, all terms defined in generally used dictionaries may not be overly interpreted.

The subject matter described herein is directed to systems and apparatuses directed to monitors (e.g., display monitors having visual electronic displays) and monitor mounts providing physical support and, in some cases, power and access to a communications/computer network. Use of such systems and apparatuses can, for example, occur in a medical environment such as the scene of a medical event, an ambulance, a hospital or a doctor's office. When a patient undergoes initial patient monitoring in such an environment, a minimum set of sensors can be connected to a patient to collect various types of patient information as described in detail herein. As a patient is moved from one area of care within the medical environment to another area of care, the patient monitor can travel with the patient. In some situations, the patient monitor can be mounted to a monitor mount to provide for stationary observation of the patient information on a visual electronic display. During the course of patient monitoring, the number of sensors can also increase due to increased testing and/or monitoring of the patient. In such a scenario, a patient monitor initially monitoring the patient can be docked into monitor mount having a second, larger monitor in order to expand the number of sensors available for patient monitoring and/or increase the number of patient parameters on a single visual electronic display by docking the smaller patient monitor within a larger patient monitor. The initial patient monitor can either remain within the larger patient monitor or be removed from the larger patient monitor.

In an exemplary implementation, the monitor mount 160 may be detachably secured to a support structure (not shown) (e.g., a wall-mounted arm) via any attachment mechanism (not shown) such as a Video Electronics Standards Association (VESA) mounting interface adapted to an attachment mechanism in a hospital room in which a patient 110 is being monitored and/or treated via one or more modules, for example one or more physiological sensors and/or medical devices. The monitor mount 160 may detachably secure the second monitor 140, and the second monitor 140 can detachably secure (or otherwise physically interface with) the first monitor 120.

Therefore, the example system provides an interconnected, versatile, and comprehensive patient care solution with a high degree of configurability. The example system acquires data at the bedside and on transport, without having to disconnect a patient as he or she is moved from care area to care area. The example system can be scaled depending on the patient's changing acuity level and medical devices can be customized to better suit hospital protocols and use models. Accordingly, the example system thereby improves clinical workflow.

Figure 8:
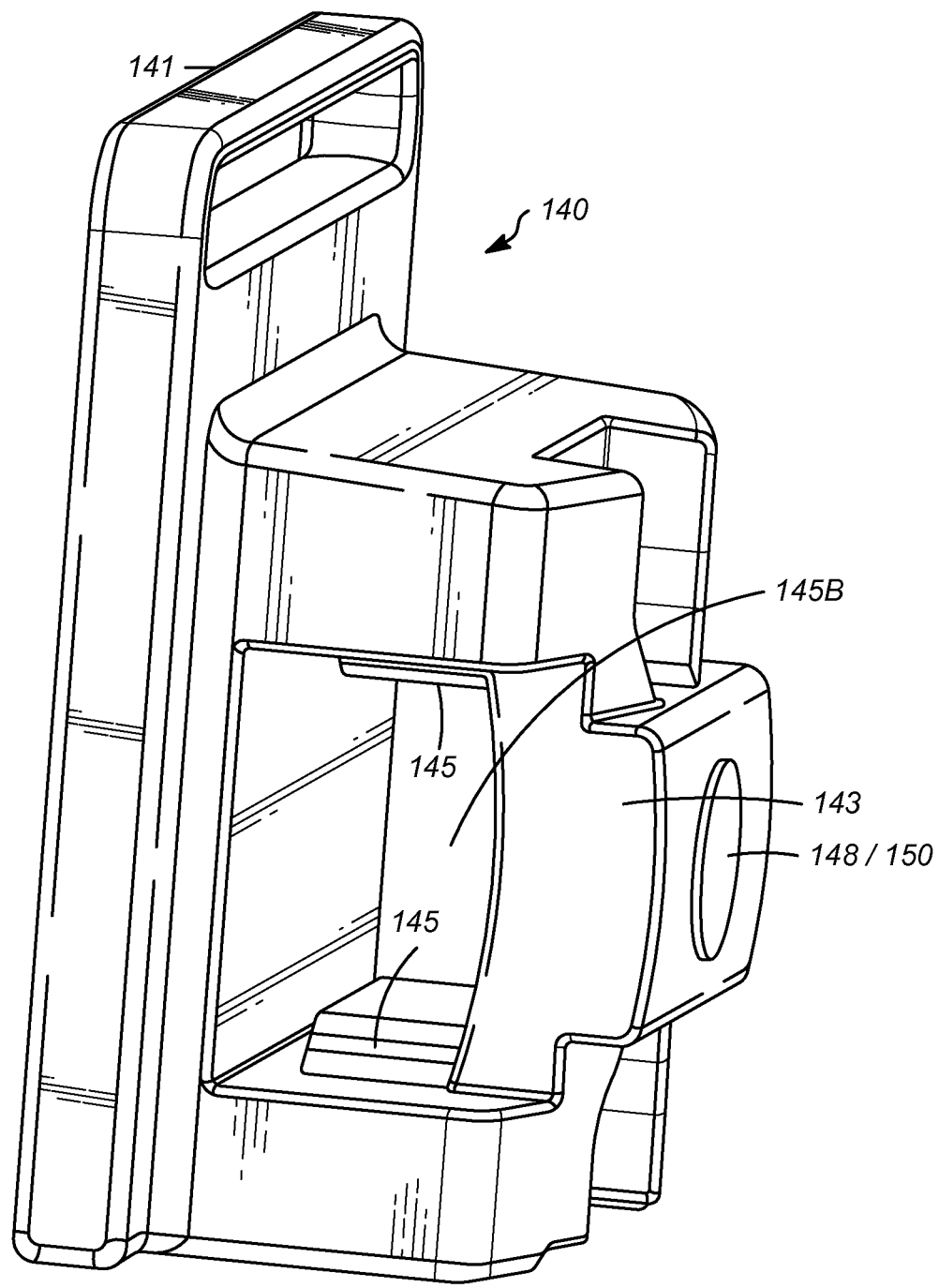
FIG. 8 is a side perspective view of a first exemplary implementation of the second monitor 140.
Figure 9:
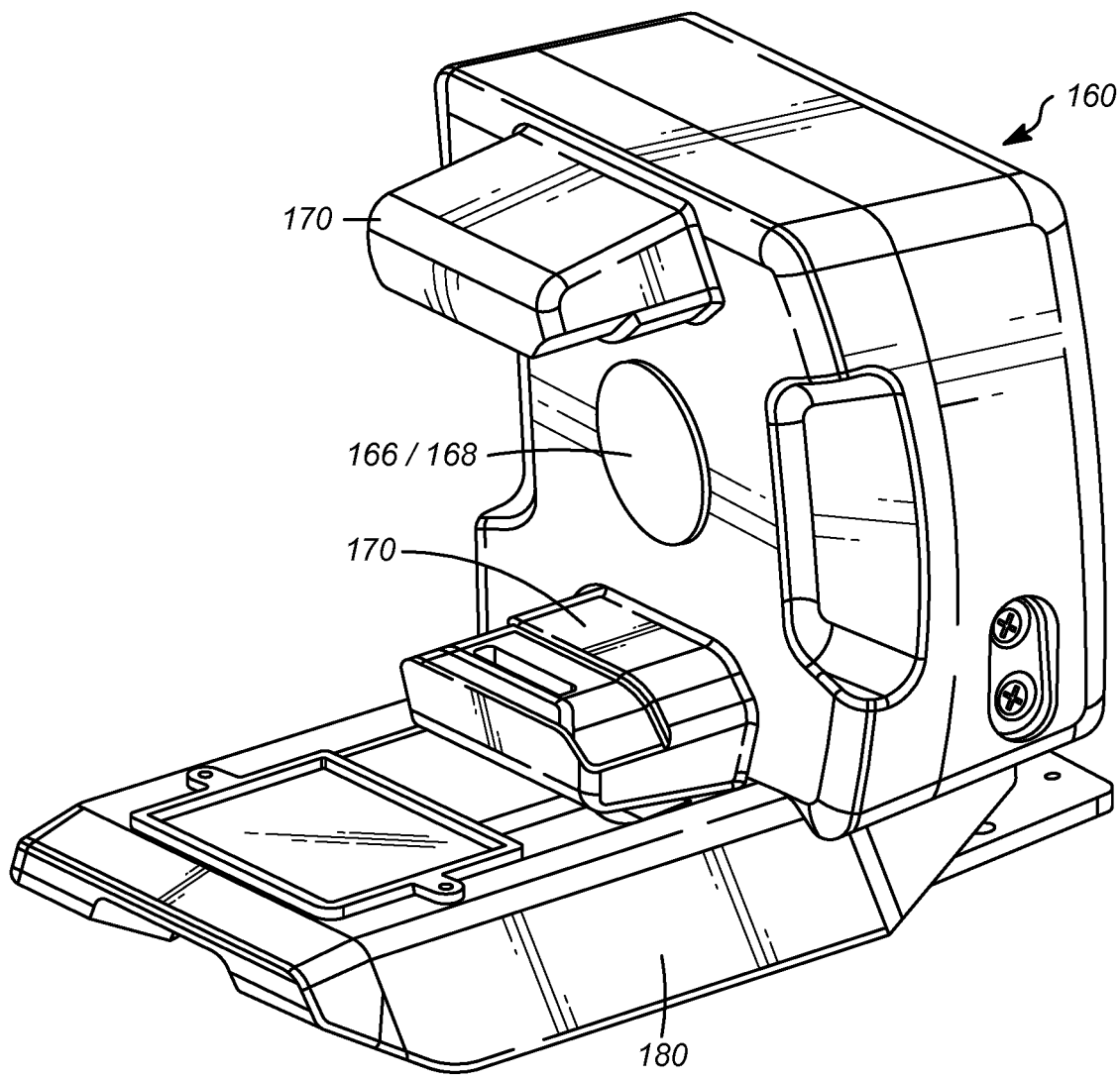
FIG. 9 is a perspective view of a second exemplary implementation of the monitor mount 160.
Figure 10:
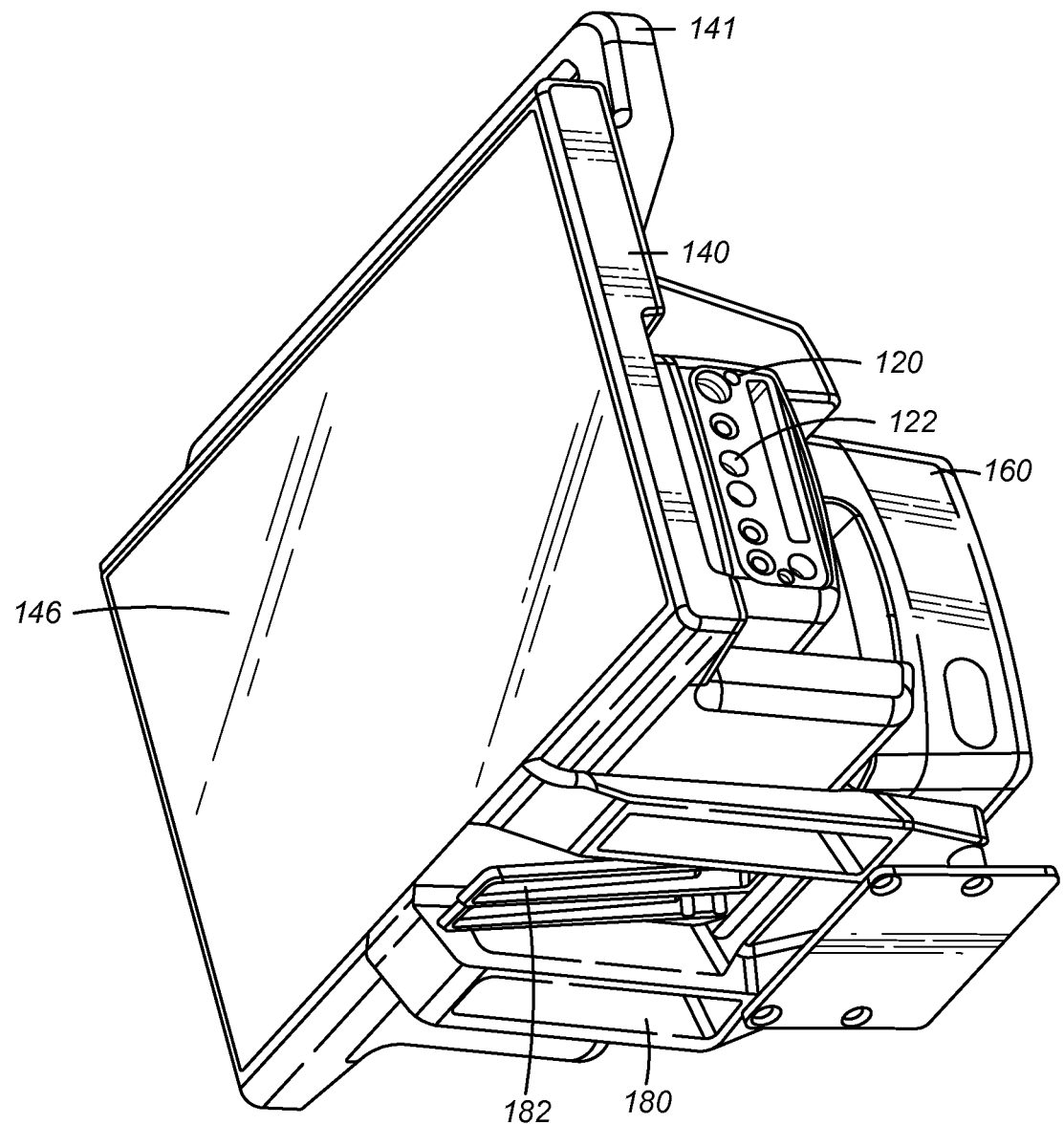
FIG. 10 is a bottom perspective view of the example system including the second exemplary implementation of the monitor mount 160 detachably securing both of the first monitor 120 and the first exemplary implementation of the second monitor 140.
Figure 11:
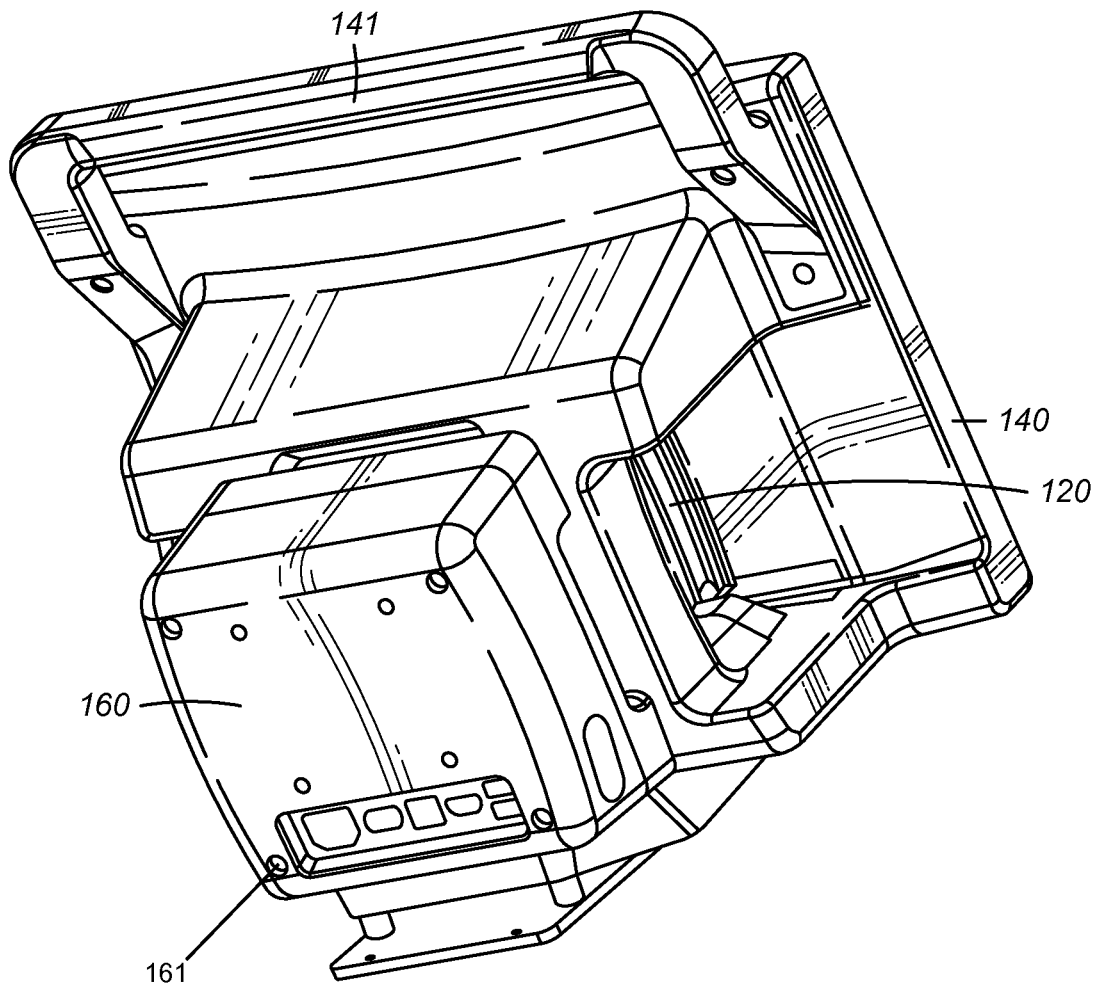
FIG. 11 is a back perspective view of the example system including the second exemplary implementation of the monitor mount 160 detachably securing both of the first monitor 120 and the first exemplary implementation of the second monitor 140.
Figure 12:
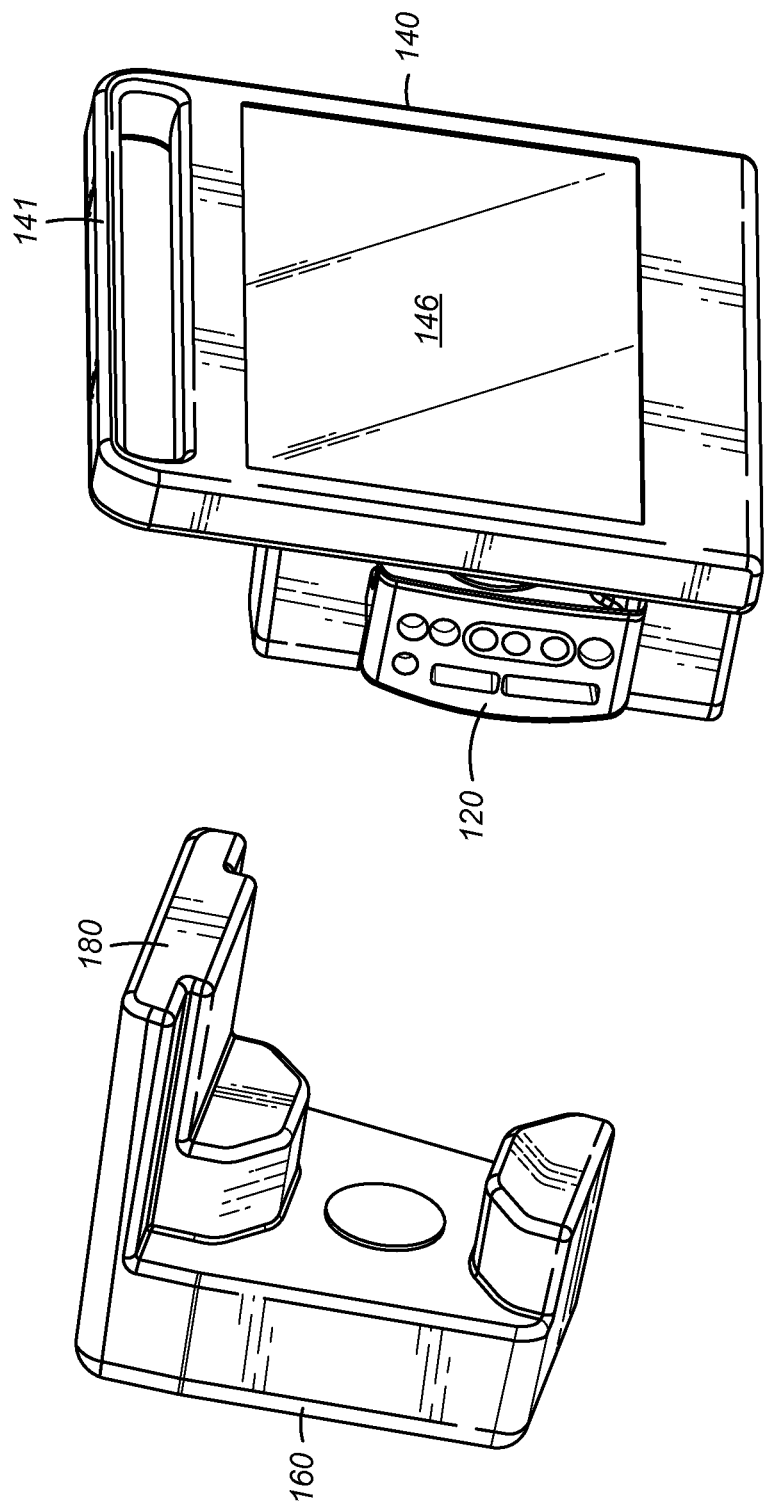
FIG. 12 is an exploded perspective view of the example system including a third exemplary implementation of the monitor mount 160, the first monitor 120 and the first exemplary implementation of the second monitor 140.
Figure 13:
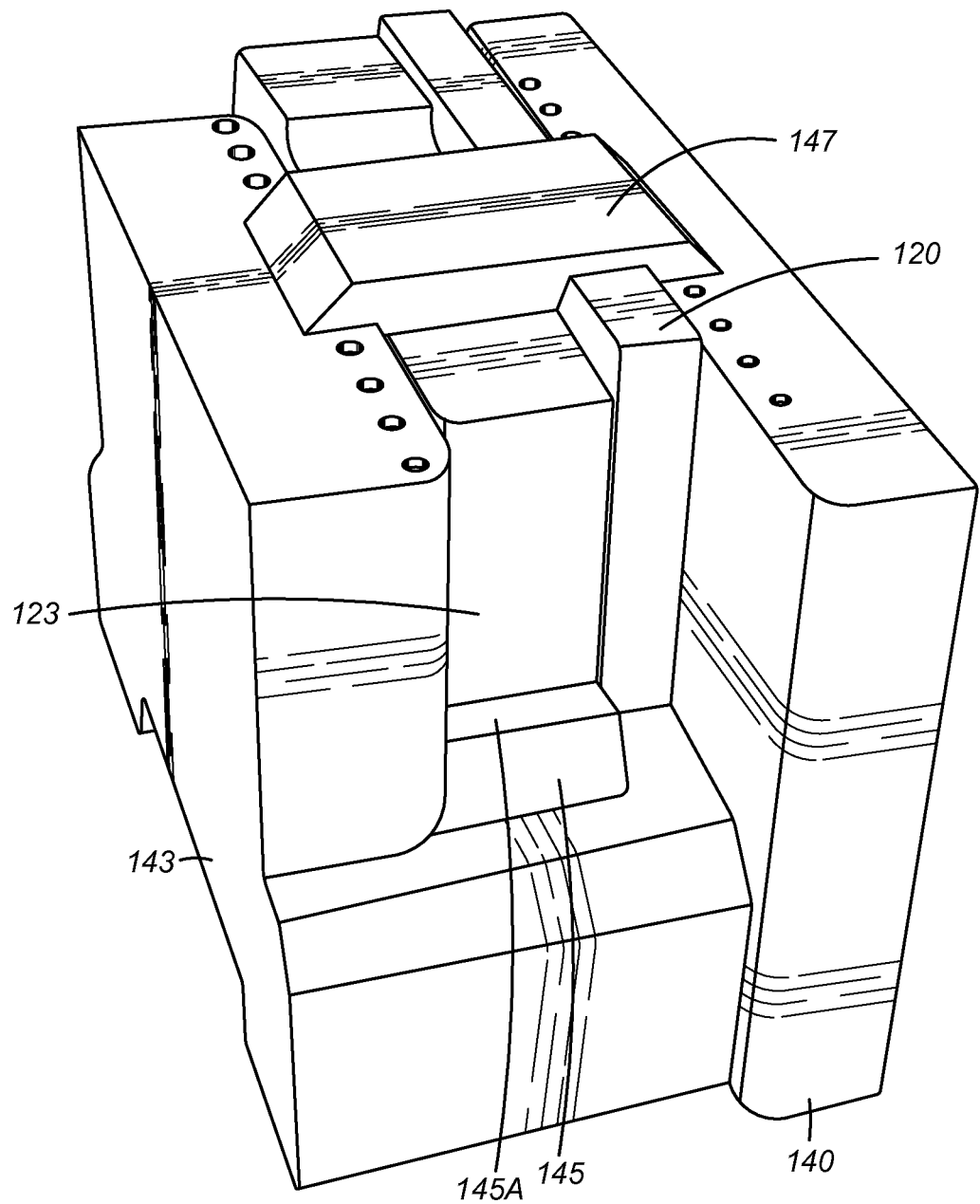
FIG. 13 is a side perspective view of a second exemplary implementation of the second monitor 140 detachably securing the first monitor 120.
Figure 14:
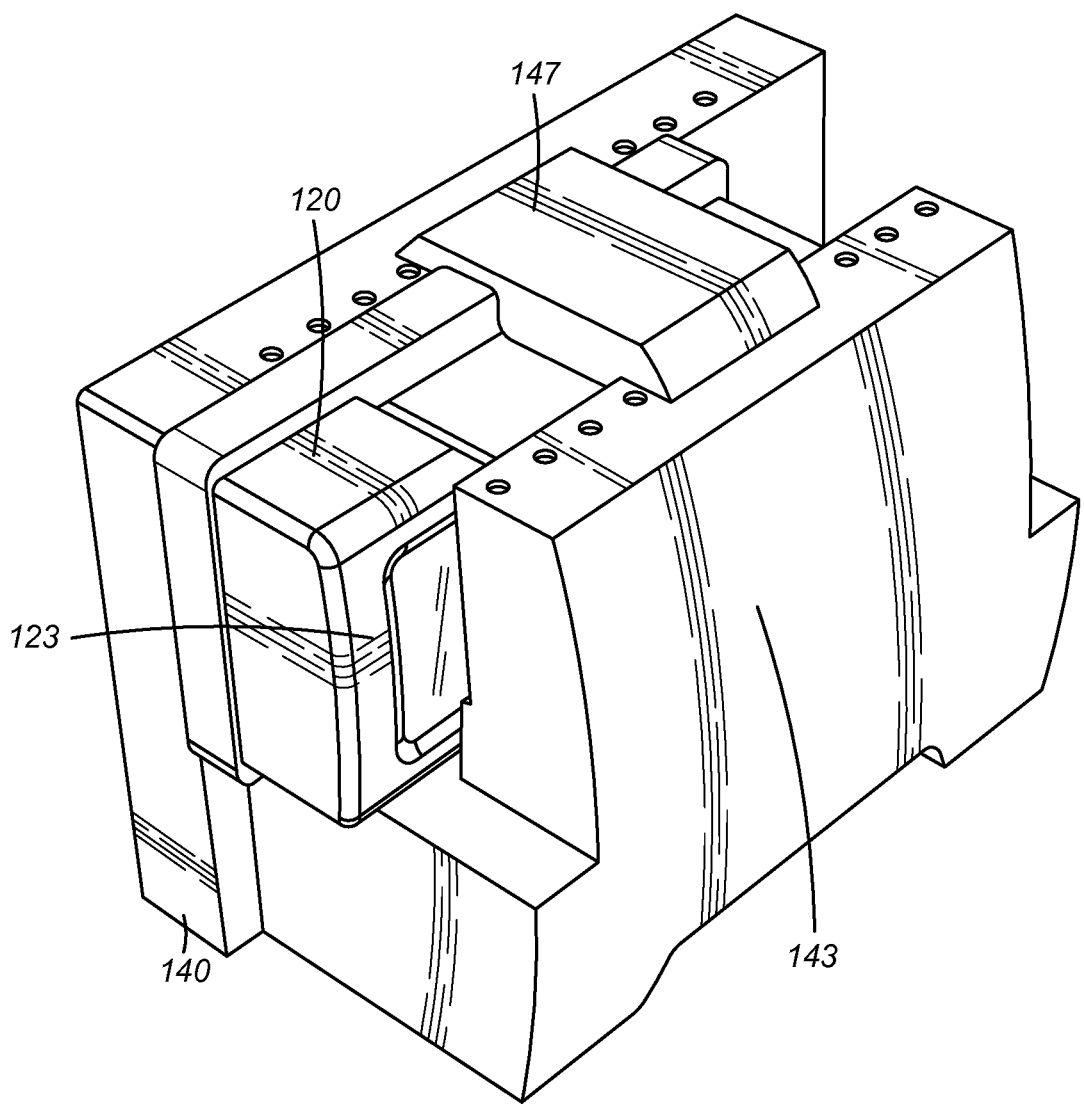
FIG. 14 is a back perspective view of the second exemplary implementation of the second monitor 140 detachably securing the first monitor 120.
Figure 15:
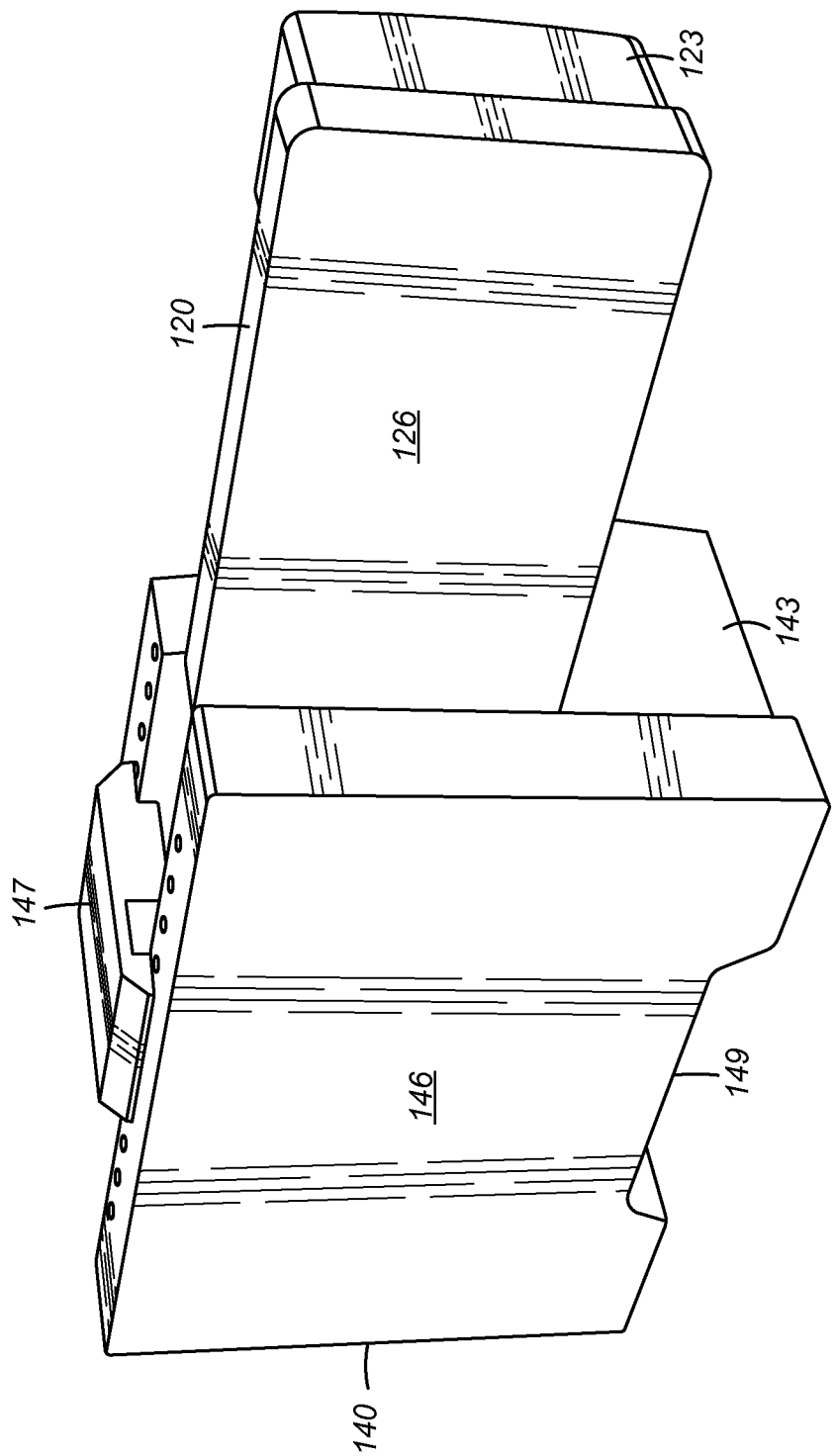
FIG. 15 is a front perspective view of the second exemplary implementation of the second monitor 140 partially receiving the first monitor 120.
Figure 16:
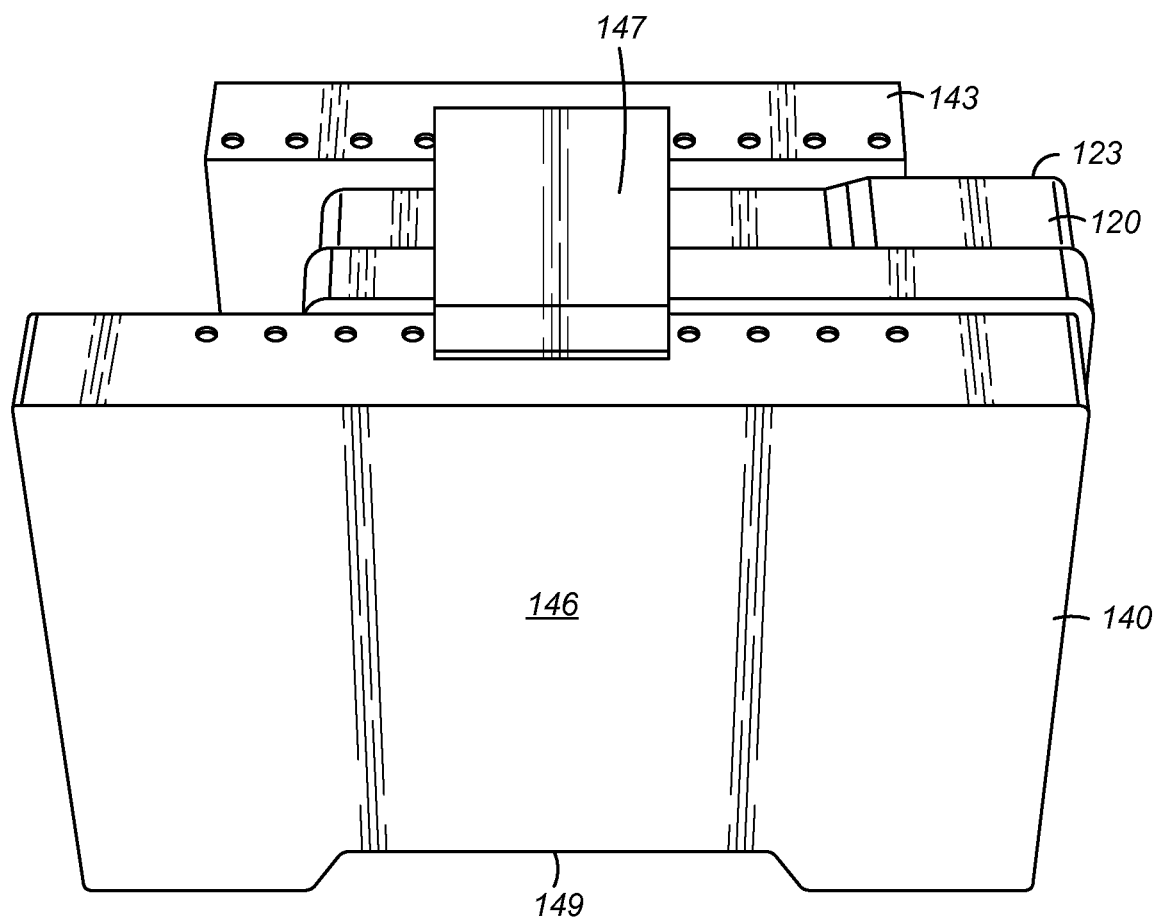
FIG. 16 is a front view of the second exemplary implementation of the second monitor 140 detachably securing the first monitor 120.

FIG. 1 is a logical diagram of a first monitor 120, a second monitor 140, and a monitor mount 160 which can detachably secure (or otherwise physically interface with) both of the first monitor 120 and the second monitor 140. FIGS. 2-8 illustrate an example system including the first monitor 120, a first exemplary implementation of the second monitor 140, and a first exemplary implementation of the monitor mount 160. FIGS. 9-11 illustrate the example system including the first monitor 120, the first exemplary implementation of the second monitor 140, and a second exemplary implementation of the monitor mount 160. FIG. 12 illustrates the example system including the first monitor 120, the first exemplary implementation of the second monitor 140, and a third exemplary implementation of the monitor mount 160. FIGS. 13-17F illustrate an example system including the first monitor 120 and a second exemplary implementation of the second monitor 140.

As will be described in further detail below, the first monitor 120 has a shape and size which differs from that of the second monitor 140. Nonetheless, both of the first monitor 120 and the second monitor 140 are able to be concurrently secured to the monitor mount 160. In addition, while certain configurations are illustrated with regard to the monitor mount 160 and the first monitor 120 and the second monitor 140, it will be appreciated that these illustrations in FIGS. 1-17F are examples and not limiting in nature (unless otherwise specified).

The first monitor 120 can, for example, be a patient monitor that is used to monitor various physiological parameters for a patient 110. With such a variation, the first monitor 120 can include a sensor interface 122 that can be used to connect via wired and/or wireless interfaces to one or more physiological sensors and/or medical devices 112 (e.g., ECG electrodes, $SPO_2$ sensor, blood pressure cuffs, apnea detection sensors, respirators, etc.) associated with the patient 110. The first monitor 120 can include one or more processors 124 (e.g., programmable data processors, etc.) which can execute various instructions stored in memory 130 of the first monitor 120. Various data and graphical user interfaces can be conveyed to a user via an electronic visual display 126 included in the first monitor 120. This information can, for example, relate to the measured physiological parameters of the patient 110 and the like (e.g., blood pressure, heart related information, pulse oximetry, respiration information, etc.). Other types of information can also be conveyed by the electronic visual display 126. In some variations, the electronic visual display 126 includes a touch screen interface that allows a user of the first monitor 120 to input data and/or modify the operation of the first monitor 120.

The first monitor 120 can additionally include a communications interface 128 which allows the first monitor 120 to directly or indirectly (via, for example, the monitor mount 160) access one or more computing networks. The communications interface 128 can include, various network cards/interfaces to enable wired and wireless communications with such computing networks. The communications interface 128 can also enable direct (i.e., device-to-device, etc.) communications (i.e., messaging, signal exchange, etc.) such as from the monitor mount 160 to the first monitor 120.

The first monitor 120 can optionally also include a power source and/or conduit 132 that can be used to power the various components of the first monitor 120 (and optionally various components of the second monitor 140 and/or the monitor mount 160). The power source/conduit 132 can include a self-contained power source such as a battery pack and/or the power source/conduit 132 can include an interface to be powered through an electrical outlet (either directly or by way of the second monitor 140 and/or the monitor mount 160). In some variations, the first monitor 120 can only be powered and render information when secured or otherwise connected to one or more of the second monitor 140 and the monitor mount 160.

Figure 5:
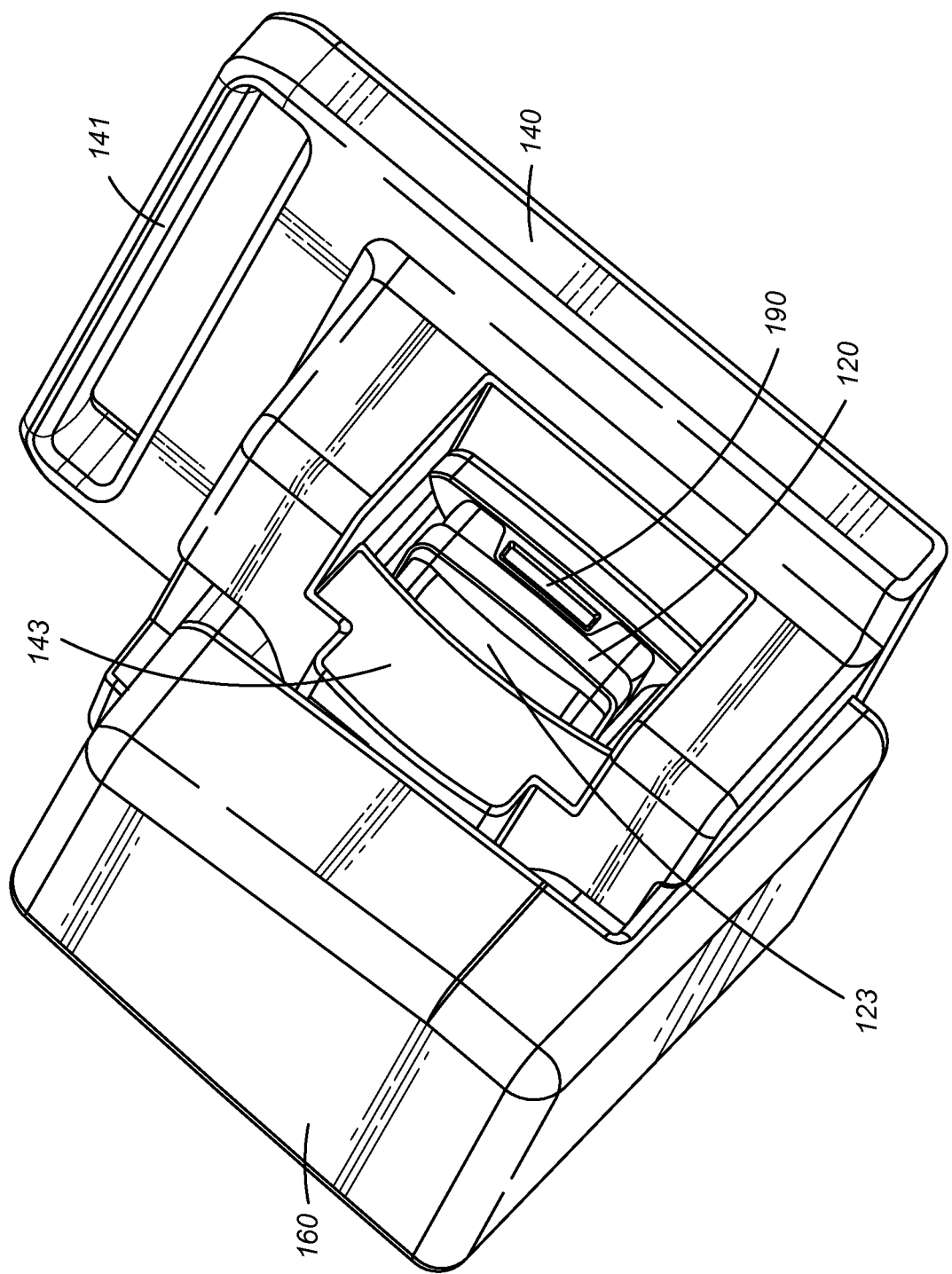
FIG. 5 is a side perspective view of the example system including the first exemplary implementation of the monitor mount 160 detachably securing both of the first monitor 120 and the first exemplary implementation of the second monitor 140.

The first monitor 120 can include a first electrical connector 190 (as shown in FIG. 5) configured to connect with a second electrical connector (not shown) of the second monitor 140 via a direct connection. When the first monitor 120 is secured with the second monitor 140, a connection is made by the first electrical connector 190 with the second electrical connector (not shown). In some variations, the first monitor 120 may not include the first electrical connector 190. Instead, the data communication between the first monitor 120 and the second monitor 140 may be wireless (e.g., optical), occurring across the communications interface 128 of the first monitor 120.

The second monitor 140 can include one or more processors 142 (e.g., programmable data processors, etc.) which can execute various instructions stored in memory 144 of the second monitor 140. Various data and graphical user interfaces can be conveyed to the user via an electronic visual display 146 included in the second monitor 140. This information can, for example, relate to the measured physiological parameters of the patient 110 and the like (e.g., blood pressure, heart related information, pulse oximetry, respiration information, thermoregulation, neonatal information, ventilator information, anesthesia information, incubation information, etc.) as received from the first monitor 120. Other types of information can also be conveyed by the electronic visual display 146. In some variations, the electronic visual display 146 includes a touch screen interface that allows a user of the second monitor 140 to input data and/or modify the operation of the second monitor 140.

The second monitor 140 can additionally include a communications interface 148 which allows the second monitor 140 to directly or indirectly (via, for example, the first monitor 120 and/or the monitor mount 160) access one or more computing networks. The communications interface 148 can include various network cards/interfaces to enable wired and wireless communications with such computing networks. The communications interface 148 can also enable direct (i.e., device-to-device, etc.) communications (i.e., messaging, signal exchange, etc.) such as from the monitor mount 160 to the second monitor 140 and the first monitor 120 to the second monitor 140.

The second monitor 140 can optionally also include a power source and/or conduit 150 that can be used to power the various components of the second monitor 140 (and optionally various components of the first monitor 120). The power source/conduit 150 can include a self-contained power source such as a battery pack and/or the power source/conduit 150 can include an interface to be powered through an electrical outlet (either directly or by way of the first monitor 120 and/or the monitor mount 160). In some variations, the second monitor 140 can only be powered and render information when secured or otherwise connected to one or more of the first monitor 120 and the monitor mount 160.

The second monitor 140 can include a second coupling 145 which is configured to detachably secure the first monitor 120. In some variations, the second coupling 145 may be positioned in a receptacle 145B (as shown in FIG. 8) of the second monitor 140. The receptacle 145B may be defined in a lateral direction of the second monitor 140 and have open side portions for receiving the first monitor 120. For example, the user can visually confirm the location of the second coupling 145 and transversely insert the first monitor 120 into the second monitor 140. In some variations, the receptacle 145B may have an open top portion instead of open side portions such that the first monitor 120 can be dropped into the second monitor 140 from above; and removed from the second monitor 140 from above.

The monitor mount 160 can include one or more processors 162 (e.g., programmable data processors, etc.) which can execute various instructions stored in memory 164 of the monitor mount 160. The monitor mount 160 can additionally include a communications interface 166 which allows the monitor mount 160 to directly or indirectly access one or more computing networks. The communications interface 166 can include various network cards/interfaces to enable wired and wireless communications with such computing networks. The communications interface 166 can also enable direct (i.e., device-to-device, etc.) communications (i.e., messaging, signal exchange, etc.) such as with the first monitor 120 and/or the second monitor 140.

The monitor mount 160 can optionally also include a power source and/or conduit 168 that can be used to power the various components of the monitor mount 160 and/or the first monitor 120 and/or the second monitor 140 when secured to the monitor mount 160. The power source/conduit 168 can include a self-contained power source such as a battery pack and/or the power source/conduit 168 can include an interface to be powered through an electrical outlet.

Any of the processors 124, 142, 162 may acquire data from any of the monitor mount 160 and one or more of the monitors 120, 140 and store the acquired data in a memory and, upon connection of the monitor mount 160 and one or more of the monitors 120, 140, transfer the data stored in the memory to the monitor mount 160 or one or more of the monitors 120, 140. The data may include any of patient identification data including information identifying a patient; patient parameter data representing at least one type of patient parameter being monitored; and device configuration data including information associated with configuration settings for the monitor mount 160 and/or the one or more monitors 120, 140.

The monitor mount 160 can optionally also include any mounting interface, such as a VESA mounting interface 161 (as shown in FIG. 11, for example) (e.g., a 75 mm or 100 mm square pattern) for mounting the monitor mount at the bedside, from the ceiling, on a wall of the room, or even outside the room for isolation purposes.

The monitor mount 160 can optionally also include an interface configured to receive a connector of a cable or wired connection for connecting a module, a monitor, other external unit or the like.

The monitor mount 160 can optionally also include one or more recesses for facilitating removal of the first monitor 120 and/or the second monitor 140.

In some variations, the one or more processors 162 and the memory 164 are omitted such that the monitor mount 160 provides only physical support and optionally a power source.

The monitor mount 160 has a shape and size which allows the monitor mount 160 to detachably secure both of the first monitor 120 and the second monitor 140 such that the respective monitors 120 and 140 can be removed by the user when desired.

Figure 2:
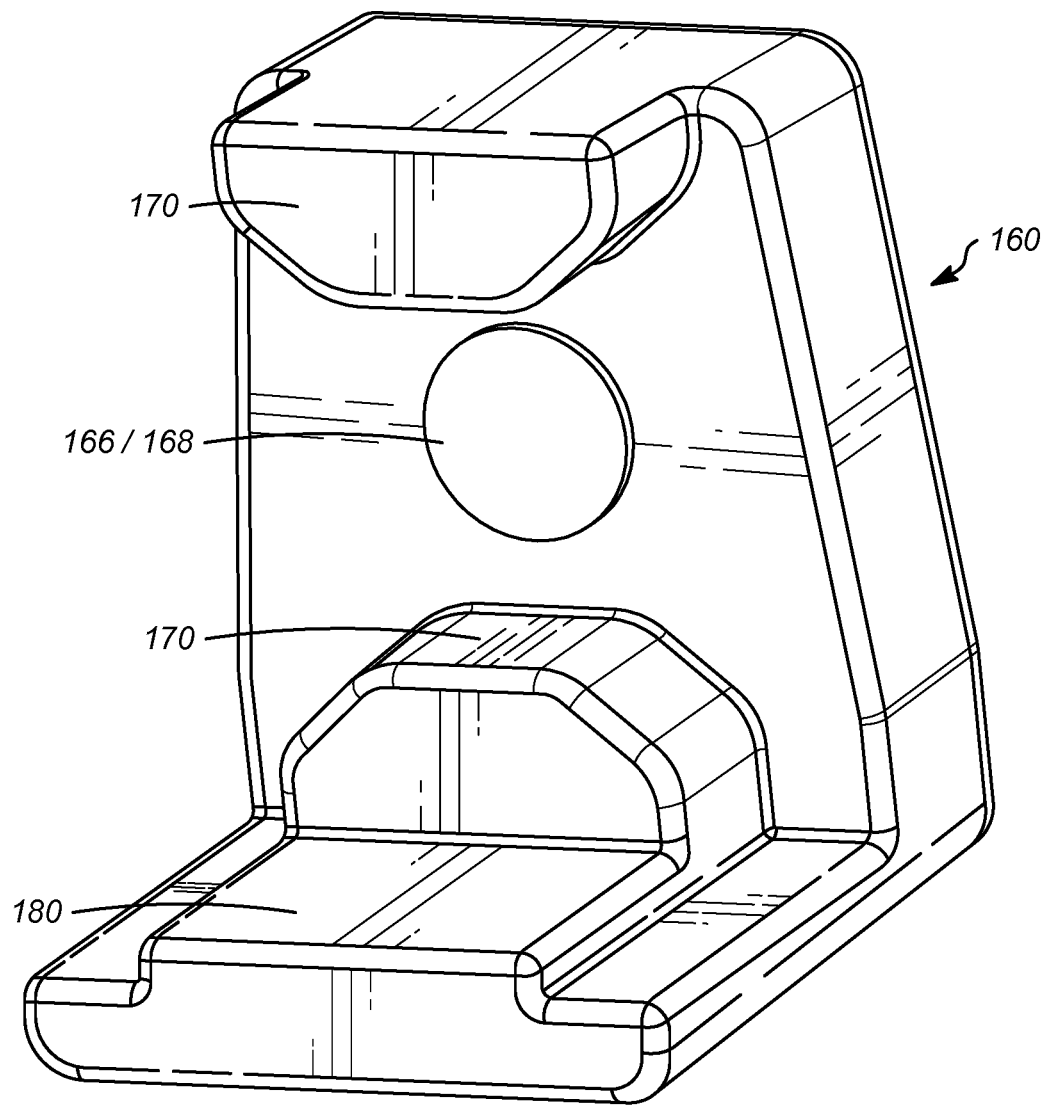
FIG. 2 is a front perspective view of a first exemplary implementation of the monitor mount 160.

The monitor mount 160 can include a first coupling 170 to allow the first monitor 120 and/or second monitor 140 to be secured to the monitor mount 160. The monitor mount 160 is able to secure each of the first monitor 120 and the second monitor 140 individually or both of the first monitor 120 and the second monitor 140 concurrently. In other words, the first coupling 170 is configured to accept either the first monitor 120 or the second monitor 140 such that the monitor mount 160 is configured to mount the first monitor 120 alone, the second monitor 140 alone, or a combination of the first monitor 120 and the second monitor 140. The first coupling 170 can include any mechanical attachment means such as a ledge, a rail, a rib, an abutment, and the like, or any combination thereof. The first coupling 170 can additionally or alternatively include different securing mechanisms including magnetic and/or electromagnetic locking mechanisms which cause the first monitor 120 to selectively be secured to the monitor mount 160. In some cases, the first monitor 120 can slide into and out of the first coupling 170 from one or more lateral directions (i.e., from one or more sides of the monitor mount 160) while in other variations, the first monitor 120 can be mounted to and removed from the front face of the monitor mount 160. In some implementations, the first monitor 120 can both slide into and out of the first coupling 170 from one or more lateral directions and be mounted to and removed from the front face of the monitor mount 160. Reference is made to FIG. 2 which shows the first coupling 170 in which the first monitor 120 can be inserted.

The positioning of the first monitor 120 when secured to the monitor mount 160 can be such that the communications interface 128 on the first monitor 120 aligns with the communications interface 166 of the monitor mount 160 to allow, for example, a direct connection (e.g., electrical connection). In other variations, the communications interface 128 of the first monitor 120 exchanges data with the communications interface 166 of the monitor mount 160 wirelessly (via, for example, optical communication by way of respective optical windows on the first monitor 120 and the monitor mount 160). The communications interface 128 of the first monitor 120 may be located on the first back portion 123 of the first monitor 120.

The positioning of the first monitor 120 when secured to the monitor mount 160 can also align the power source/conduit 132 of the first monitor 120 to be coupled to the power source/conduit 168 of the monitor mount 160 which causes the monitor mount 160 to power the first monitor 120.

The monitor mount 160 can include a support portion 180 to allow the second monitor 140 to be secured to the monitor mount 160. The support portion 180 may be positioned at a top of the monitor mount 160 or a bottom of the monitor mount 160. The support portion 180 can include any mechanical attachment means such as a ledge, a rail, a rib, an abutment, and the like, or any combination thereof. The positioning of the second monitor 140 when secured to the monitor mount 160 can be such that the communications interface 148 on the second monitor 140 aligns with the communications interface 166 of the monitor mount 160 to allow, for example, a direct connection (e.g., electrical connection). In other variations, the communications interface 148 of the second monitor 140 exchanges data with the communications interface 166 of the monitor mount 160 wirelessly (via, for example, optical communication by way of respective optical windows on the second monitor 140 and the monitor mount 160). The communications interface 148 of the second monitor 140 may be located on the second back portion 143 of the second monitor 140.

The support portion 180 can enable front-to-back docking of the second monitor 140 within monitor mount 160 by providing a shelf or similar feature extending outwardly. This feature of the support portion 180 can support and/or disperse the weight of the second monitor 140 during positioning of the second monitor 140. For example, a user attempting to position the second monitor 140 within the monitor mount 160 can rest the second monitor 140 on the support portion 180 during the positioning while attaching the second back portion 143 of the second monitor 140 to the first coupling 170. The support portion 180 can support a bottom face of the second monitor 140.

Alternatively or additionally, as shown in FIG. 12, the support portion 180 can enable hanging or suspension of a handle 141 of the second monitor 140 from the monitor mount 160 by providing any mechanical attachment means such as a ledge, a rail, a rib, an abutment, and the like, or any combination thereof extending laterally from the top portion of mount 160. This feature of the support portion 180 can support and/or disperse the weight of the second monitor 140 during positioning of the second monitor 140. For example, a user attempting to position the second monitor 140 within the monitor mount 160 can hang or suspend the handle 141 of the second monitor 140 from the support portion 180 during the positioning while attaching the second back portion 143 of the second monitor 140 to the first coupling 170.

The positioning of the second monitor 140 when secured to the monitor mount 160 can also align the power source/conduit 150 of the second monitor 140 to be coupled to the power source/conduit 168 of the monitor mount 160 which causes the monitor mount 160 to power the second monitor 140 or vice-versa. In some variations, the positioning of the second monitor 140 when secured to the monitor mount 160 and/or when the first monitor 120 is also secured to the monitor mount 160 can also align the power source/conduit 150 of the second monitor 140 to be coupled to the power source/conduit 132 of the first monitor 120 (which in turn is connected to the power source/conduit 168 of the monitor mount 160) which causes the first monitor 120 to power the second monitor 140.

FIG. 2 is a front perspective view that shows a first exemplary implementation of the monitor mount 160. As illustrated in FIG. 2, the monitor mount 160 includes the first coupling 170 and the support portion 180. The communications interface 166 and the power/source conduit 168 can be positioned intermediate of the first coupling 170 so that the first monitor 120 or the second monitor 140 may interface therewith. Similarly, the communications interface 166 and the power/source conduit 168 can alternatively be included as part of the support portion 180 so that the second monitor 140 may interface therewith at that location. In some variations, communications interface 166 can be a wireless (e.g., optical) interface providing wireless (e.g., optical) communications between the monitor mount 160 and the first monitor 120, between the monitor mount 160 and the second monitor 140, and/or between the first monitor 120 and the second monitor 140 coupled together. FIG. 2 also shows various aspects of the monitor mount 160 including details about how the first monitor 120 can be transversely inserted into the monitor mount 160 (i.e., the first monitor 120 can slide into the monitor mount 160) between the two portions of the first coupling 170.

Figure 3:
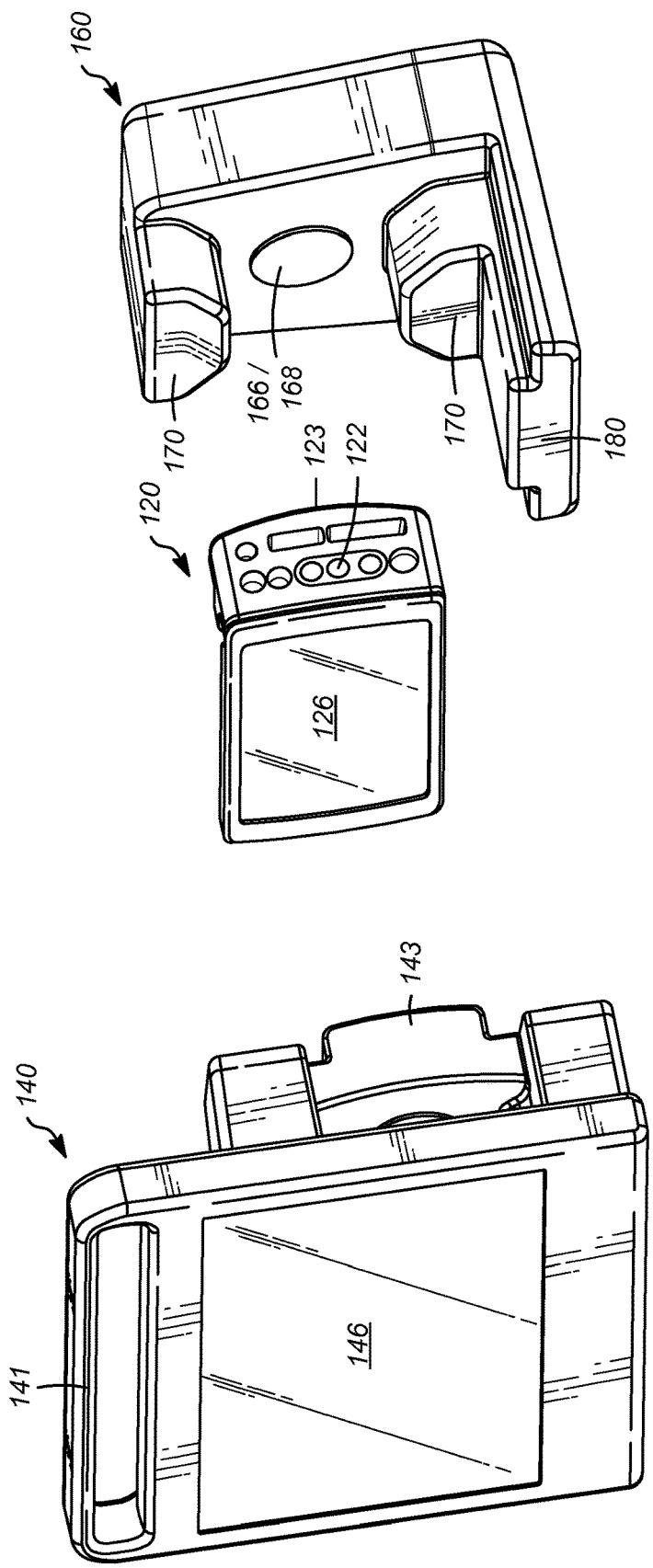
FIG. 3 is an exploded perspective view of an example system including the first monitor 120, a first exemplary implementation of the second monitor 140, and the first exemplary implementation of the monitor mount 160.

FIG. 3 is an exploded perspective view that shows the relationship among the first monitor 120, the second monitor 140, and the first exemplary implementation of the monitor mount 160. The first back portion 123 of the first monitor 120 or the second back portion 143 of the second monitor 140 can be detachably secured to the first coupling 170. The first monitor 120 can also be detachably secured to the second coupling 145 of the second monitor 140.

Figure 4:
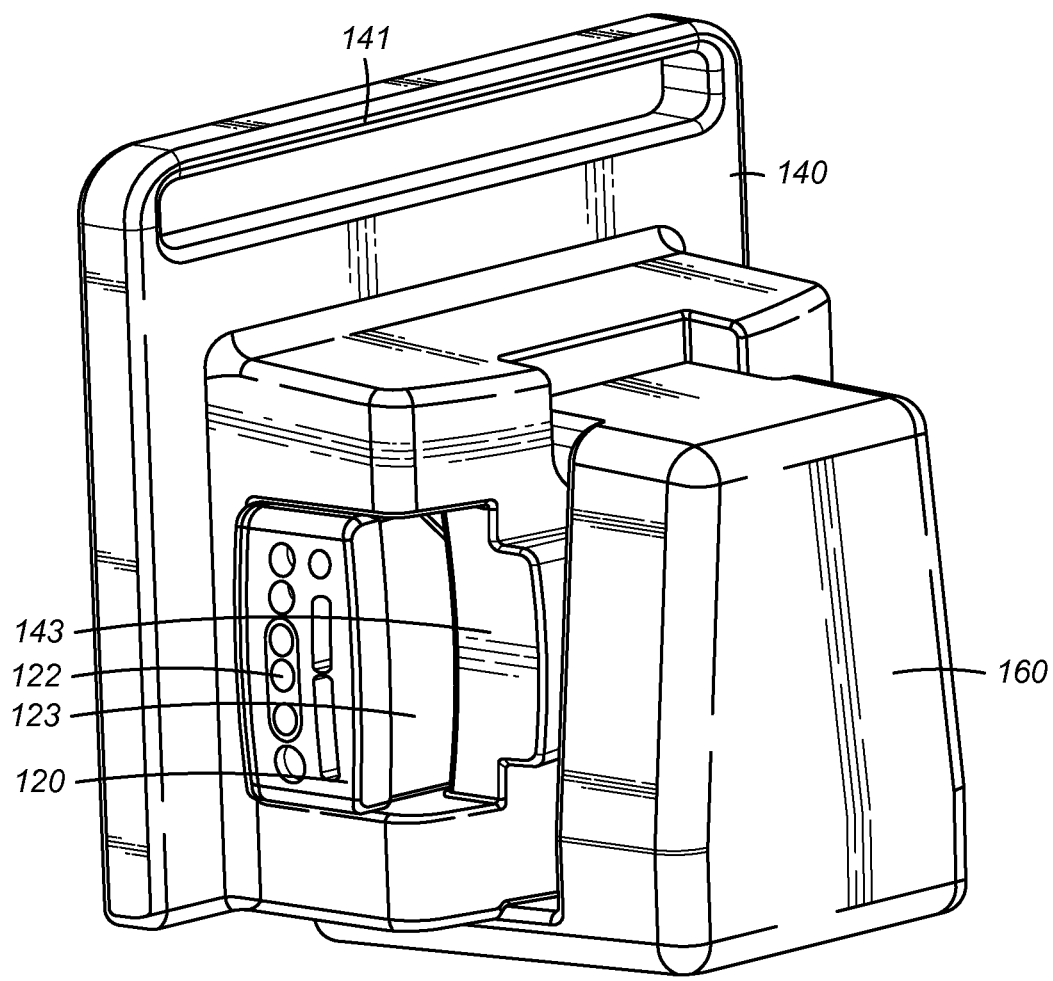
FIG. 4 is a side perspective view of the example system including the first exemplary implementation of the monitor mount 160 detachably securing both of the first monitor 120 and the first exemplary implementation of the second monitor 140.

FIG. 4 is a side perspective view showing the relationship among the first monitor 120, the second monitor 140, and the first exemplary implementation of the monitor mount 160 when all the units are connected. As illustrated in FIG. 4, the second back portion 143 of the second monitor 140 is detachably secured to the first coupling 170 of the monitor mount 160 and the first monitor 120 is detachably secured to the second coupling 145 of the second monitor 140. In some variations, as is illustrated in FIG. 4, a portion such as a back portion of the second monitor 140 can surround/obscure at least a portion of the first monitor 120; such portion of the first monitor 120 may include some or all of the electronic visual display 126 of the first monitor 120. The first monitor 120 can be removed from the monitor mount 160 independently of the second monitor 140 (for example, with reference to FIG. 4, by being removed transversely from the monitor mount 160). In addition, the monitor mount 160 can be arranged to allow left side and/or right side transverse removal of the first monitor 120 from the monitor mount 160. The second monitor 140 can be arranged to allow left side and/or right side transverse removal of the first monitor 120 from the second monitor 140. In still other variations, the second monitor 140 with the first monitor 120 disposed therein can be removed from the monitor mount 160. Stated differently, the combination of the first monitor 120 and the second monitor 140 can together be detached from the monitor mount 160. In some variations, the second monitor 140 can have a shape and size to completely envelop and secure the first monitor 120 within the receptacle 145B. The first monitor 120 can be secured and interface within the second coupling 145 in the receptacle 145B of the second monitor 140. In some variations, when the first monitor 120 is mounted within the receptacle 145B of the second monitor 140, the communications interface 148 (e.g., optical communications interface), and optionally the power source/conduit 150, on the second monitor 140 provide data communications with, and optionally power to, the first monitor 120 via the communications interface 128 (e.g., optical communications interface), and optionally the power source/conduit 132, on the first monitor 120 within the receptacle 145B.

For example, with such an arrangement, data that otherwise would have been displayed by the electronic visual display 126 of the first monitor 120 can be displayed by the electronic visual display 146 of the second monitor 140.

Therefore, the monitor mount 160 of the present disclosure is capable of mixed use with monitors 120, 140 having different sizes which are interoperable with the same controller and the same user interface, and which can be universally docked to the monitor mount 160.

FIG. 5 is another side perspective view showing the relationship among the first monitor 120, the second monitor 140, and the first exemplary implementation of the monitor mount 160. As illustrated in FIG. 5, the second back portion 143 of the second monitor 140 is detachably secured to the first coupling 170 and the first monitor 120 is detachably secured to the second coupling 145. The first monitor 120 may include the first electrical connector 190.

Figure 6:
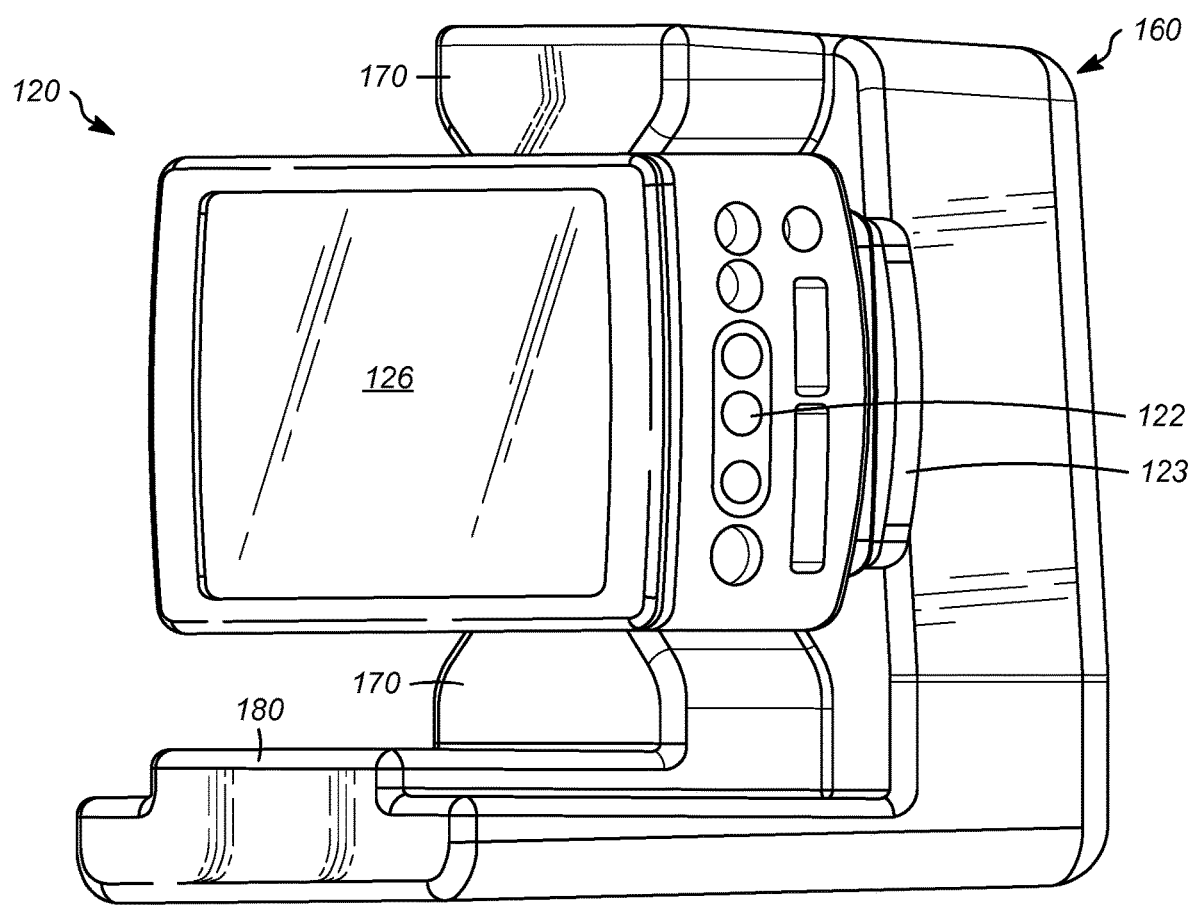
FIG. 6 is a front perspective view of the first exemplary implementation of the monitor mount 160 detachably securing the first monitor 120.

FIG. 6 is a front perspective view showing the relationship between the first monitor 120, and the first exemplary implementation of the monitor mount 160 without the second monitor 140 being present. In FIG. 6, the first back portion 123 of the first monitor 120 is detachably secured to the first coupling 170.

Figure 7:
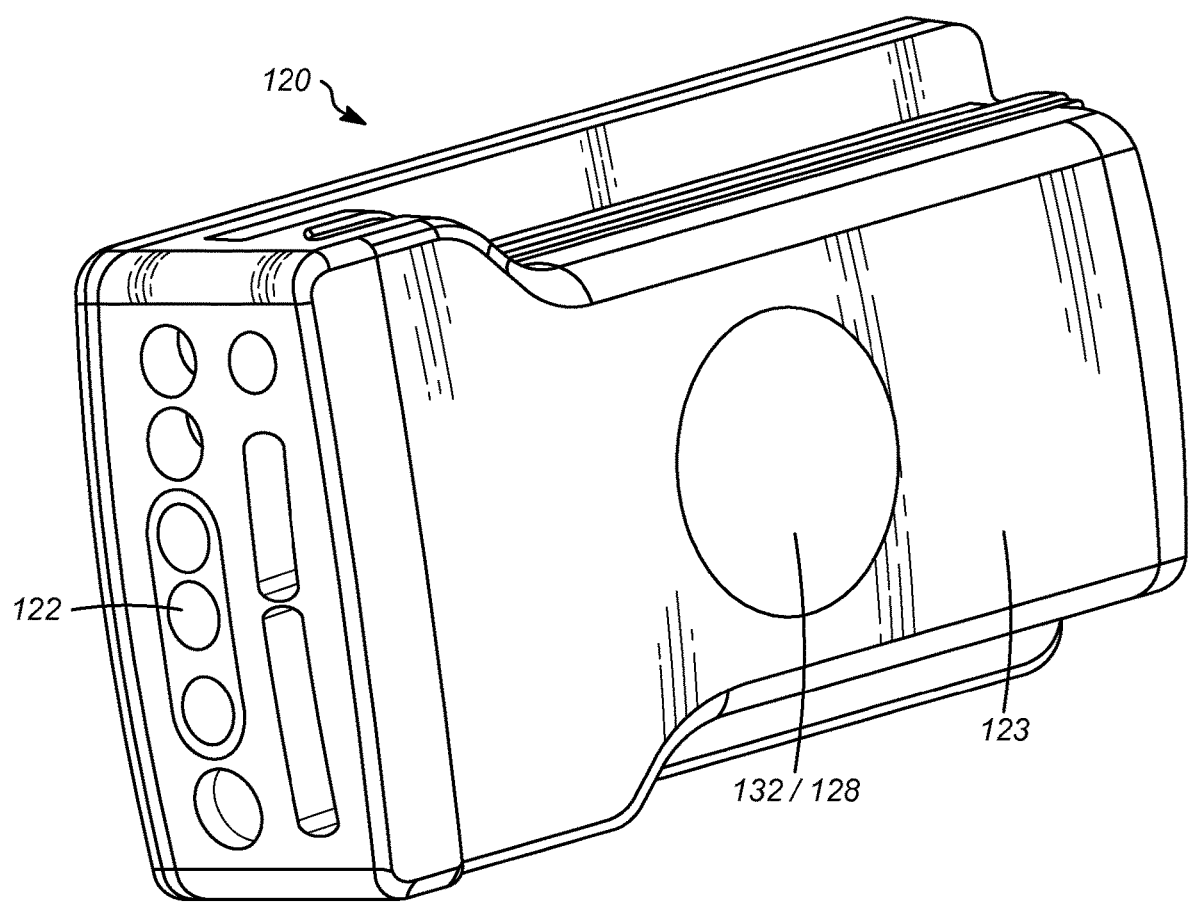
FIG. 7 is a back perspective view of an exemplary implementation of the first monitor 120.

FIG. 7 is a back perspective view of the first monitor 120. As illustrated in FIG. 7, the first monitor 120 has the sensor interface 122, the first back portion 123, the power source and/or conduit 132, and the communications interface 128. The first monitor 120 may include one or more of a groove, a slit, an aperture, a rib, a wall portion, a ridge, an abutment, or the like for facilitating the transverse insertion and/or removal of the first monitor 120 into the receptacle 145B of the second monitor 140 and/or into the first coupling 170 of the monitor mount 160.

FIG. 8 is a side perspective view of the second monitor 140. As illustrated in FIG. 8, the second monitor 120 has the handle 141, the second back portion 143, the second coupling 145, the communications interface 148, and the power source and/or conduit 150. The handle 141 can facilitate the detachable securing of the second monitor 140 to the support portion 180 (as shown in FIG. 12) and/or the first coupling 170. The second coupling 145 can have one or more guiding surfaces 145A for facilitating the transverse insertion and/or removal of the first monitor 120 into the receptacle 145B of the second monitor 140.

FIG. 9 is a front perspective view that shows a second exemplary implementation of the monitor mount 160. As illustrated in FIG. 9, the monitor mount 160 includes the first coupling 170 and the support portion 180. The communications interface 166 and the power/source conduit 168 can be positioned intermediate the first coupling 170 so that the first monitor 120 may interface therewith. Similarly, the communications interface 166 and the power/source conduit 168 can alternatively be included as part of the support portion 180 so that the second monitor 140 may interface therewith. Further, the monitor mount 160 includes recesses on either side of the first coupling 170 that can facilitate coupling/uncoupling of the first monitor 120 and/or the second monitor 140 to/from the monitor mount 160.

FIG. 10 is a bottom perspective view that shows the relationship among the first monitor 120, the second monitor 140, and the second exemplary implementation of the monitor mount 160. As illustrated in FIG. 10, the support portion 180 of the monitor mount 160 can additionally include a release mechanism 182 which causes the second monitor 140 to selectively be released from the monitor mount 160.

FIG. 11 is a back perspective view that shows the relationship among the first monitor 120, the second monitor 140, and the second exemplary implementation of the monitor mount 160.

FIG. 12 is an exploded perspective view showing the relationship between the third exemplary implementation of the monitor mount 160 and the first exemplary implementation of the second monitor 140 detachably securing the first monitor 120.

Figure 17A:
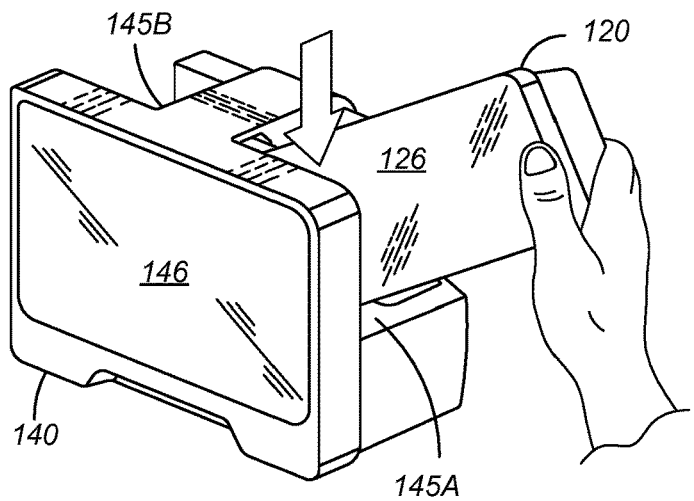
FIGS. 17A-17C are side perspective views of a first exemplary sequence of the first monitor 120 being detachably secured in the second exemplary implementation of the second monitor 140.
Figure 17B:
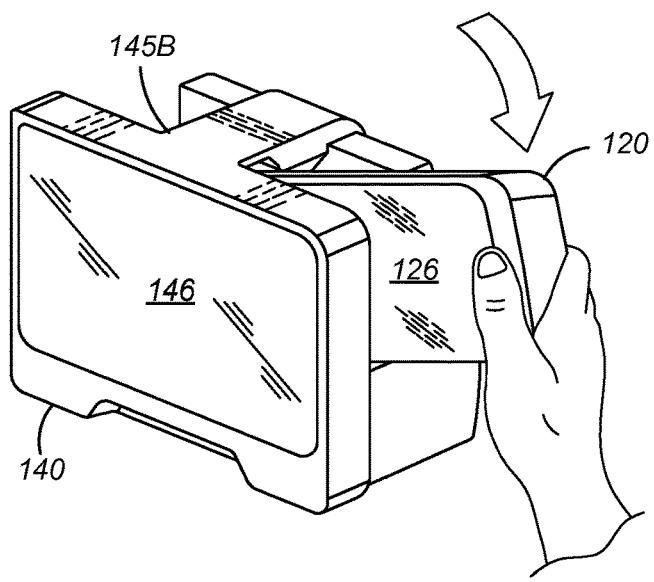
Figure 17C:
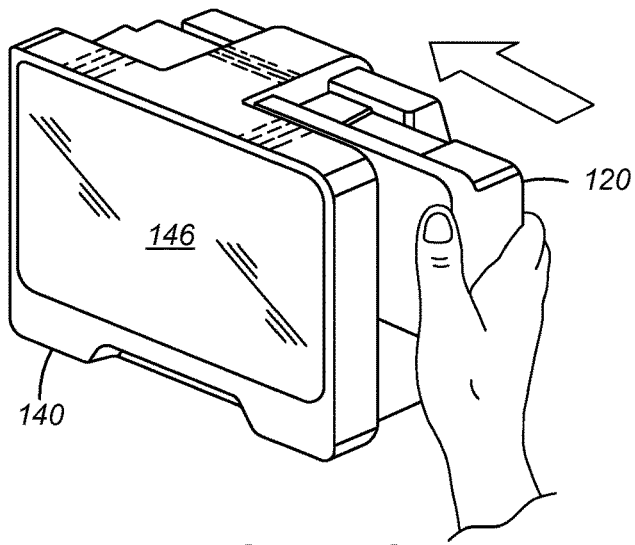
Figure 17D:
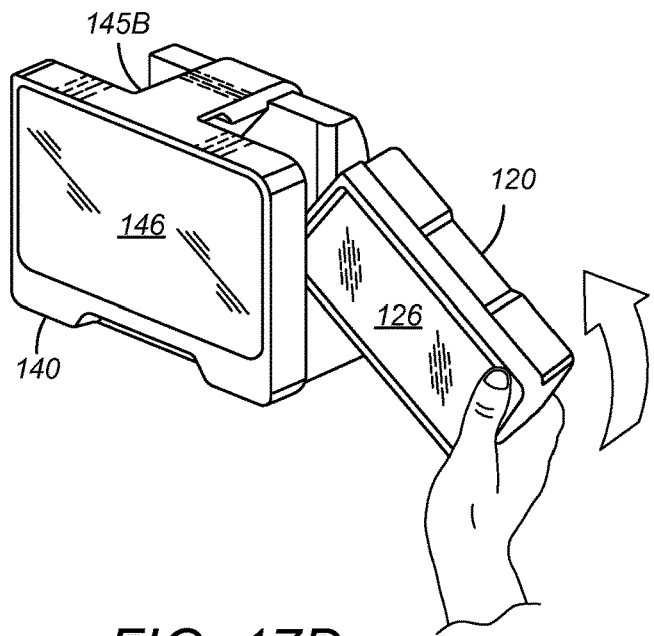
FIGS. 17D-17F are side perspective views of a second exemplary sequence of the first monitor 120 being detachably secured in the second exemplary implementation of the second monitor 140.
Figure 17E:
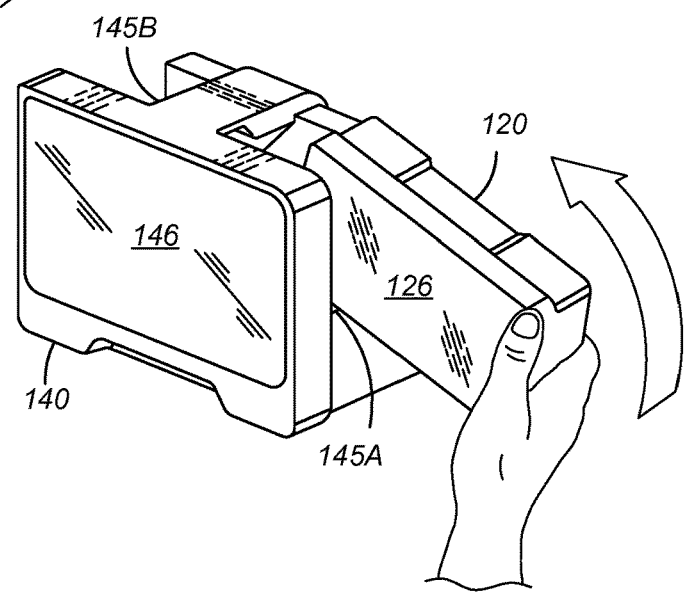
Figure 17F:
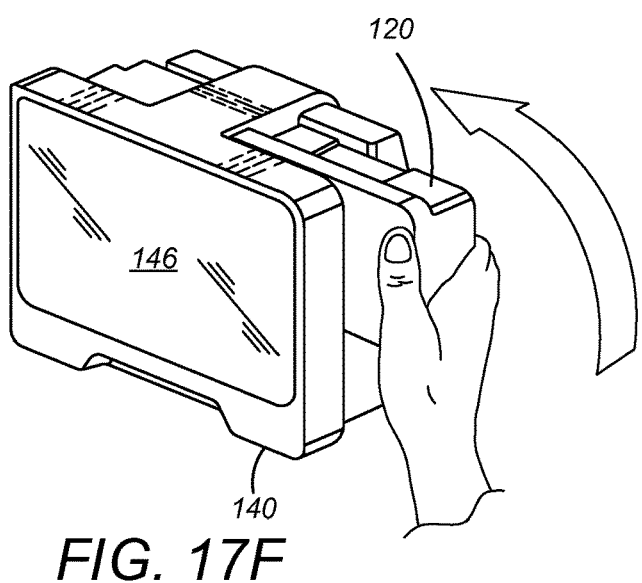

FIGS. 13-17F show the second exemplary implementation of the second monitor 140 detachably securing the first monitor 120. The second monitor 140 may include a second electronic visual display 146 and a receptacle 145B including the second coupling 145, a bridge portion 147 and two parallel surfaces 149. The bridge portion 147 may connect the two parallel surfaces 149 and extend over the first monitor 120 when the first monitor 120 is secured in the second monitor 140. A width of the bridge portion 147 in a lateral direction of the second monitor 140 may be less than a width of the second monitor 140 in the lateral direction of the second monitor 140. Furthermore, a width of the bridge portion 147 in the lateral direction of the second monitor 140 may be less than a width of the first monitor 120 in a lateral direction of the first monitor 120. In other words, the width of the receptacle 145B in these variations can be less than the width of the receptacle 145B in other variations. Such decreased receptacle width facilitates self-location of the first monitor 120 by the user. For example, the user can hold the first monitor 120 overhead, and without visually confirming the location of the second coupling 145, insert the first monitor 120 such that the first monitor 120 contacts at least one guiding surface 145A of the second coupling 145 and slides into a position in which the first monitor 120 is detachably secured in the second monitor 140. Stated differently, the at least one guiding surface 145A of the second coupling 145 is configured to initially receive the first monitor 120 and guide the first monitor 120 to a secured position within the second monitor 140. As a first example, as shown in FIGS. 17A-17C, the first monitor 120 can be inserted downwardly from above into the receptacle 145B of the second monitor 140 by first holding the first monitor 120 at a downward angle against a floor (i.e., the at least one guiding surface 145A) of the receptacle 145B, and thereafter the first monitor 120 can be rotated downwardly and into the second monitor 140. As a second example, as shown in FIGS. 17D-17F, the first monitor 120 can be inserted upwardly from below into the receptacle 145B of the second monitor 140 by first holding the first monitor 120 at an upward angle against the floor (i.e., the at least one guiding surface 145A) of the receptacle 145B, and thereafter the first monitor 120 can be rotated upwardly and into the second monitor 140. This provides an advantage over a full-width receptacle because it is difficult to align a first monitor 120 with a full-width receptacle if the full-width receptacle is overhead. Such insertion and removal can be performed with one hand by the user. In other words, it is not necessary to perform two separate motions to insert or remove the first monitor 120 from the second monitor 140. In some variations not shown, the receptacle may have an open top portion instead of open side portions such that the first monitor 120 can be dropped into the second monitor 140 from above; and removed from the second monitor 140 from above. The first monitor 120 may be received in the receptacle 145B of the second monitor 140 such that the first monitor 120 is adjacent to the bridge portion 147, the two parallel surfaces 149, and the second coupling 145. A floor of the receptacle 145B may include the second coupling 145. Furthermore, the second coupling 145 may include at least one guiding surface 145A configured to initially receive the first monitor 120 at an angle such that the first monitor 120 is rotated and thereafter guide the first monitor 120 to a secured position within the second monitor 140. The bridge portion 147 may include a lateral slot and a top portion of the first monitor 120 may be transversely inserted into the lateral slot. The second monitor 140 may also include a handle and the bridge portion 147 and the handle may be formed as a single unit. In some variations, a top portion of the second monitor 140 may include holes for repositioning the bridge portion 147.

A module (not shown) can provide one or more different functions used in delivering healthcare to a patient. The module can acquire patient data including the monitored parameters allocated to a given patient from a network and collate the information for storage in a database. The module can be any of a patient monitoring module for acquiring and processing data generated by at least one physiological sensor monitoring a physiological parameter of a patient (e.g., gas measurement, end-tidal carbon dioxide ($etCO_2$), SCIO, patient gas, thermoregulation, blood pressure, heart related measurement, pulse oximetry, respiration, neonatal measurement, ventilation, anesthesia information, incubation information, etc.), a patient treatment module for delivering treatment to the patient (e.g., monitoring fluids administered to the patient and supplying anesthesia to the patient, respectively), a control module, a charging module, a compartment module, a converter module, a transmitter module, a relay module, a battery module, a camera module, a purge module, a robot module, an internal and/or external communication module, a power supply module, a global positioning system (GPS) module, a mobile and/or stationary data transfer module, an output board, a facility module, an output board, a dock module, an adapter module, a passive treatment module, an active treatment module, etc. A processor can process signals derived from the module. In the embodiment depicted in FIG. 1, a processor 162 in a monitor mount 160, a processor 124 in a (first) monitor 120 and/or a processor 142 in another (second) monitor 140 can process signals derived from the module. The monitor mount 160, and the monitors 120, 140 communication interface provide bidirectional communication between the corresponding processor and the module via a network.

Although various embodiments have been described above, these are to be regarded as merely examples. Accordingly, those of ordinary skill in the art will recognize that various changes and modifications of the examples described herein can be made without departing from the spirit and scope of the present disclosure. For example, any feature of any particular portion, embodiment or modification of the monitors 120, 140 may be included or omitted from any of the other portions, embodiments or modifications of the monitors 120, 140. Any feature of any particular portion, embodiment or modification of the monitor mount 160 may be included or omitted from any of the other portions, embodiments or modifications of the monitor mount 160.

Further, it is noted that the present disclosure may be implemented as any combination of a system, an integrated circuit, and a computer program on a non-transitory computer readable recording medium. The processor and any other parts of the computing system may be implemented as Integrated Circuits (IC), Application-Specific Integrated Circuits (ASIC), or Large Scale Integrated circuits (LSI), system LSI, super LSI, or ultra LSI components which perform a part or all of the functions of the computing system.

Each of the parts of the present disclosure can be implemented using many single-function components, or can be one component integrated using the technologies described above. The circuits may also be implemented as a specifically programmed general purpose processor, CPU, a specialized microprocessor such as Digital Signal Processor that can be directed by program instructions on a memory, a Field Programmable Gate Array (FPGA) that can be programmed after manufacturing, or a reconfigurable processor. Some or all of the functions may be implemented by such a processor while some or all of the functions may be implemented by circuitry in any of the forms discussed above.

The present disclosure may be implemented as a non-transitory computer-readable recording medium having recorded thereon a program embodying methods/algorithms for instructing the processor to perform the methods/algorithms. The non-transitory computer-readable recording medium can be, for example, a CD-ROM, DVD, Blu-ray disc, or an electronic memory device.

Each of the elements of the present disclosure may be configured by implementing dedicated hardware or a software program on a memory controlling a processor to perform the functions of any of the components or combinations thereof. Any of the components may be implemented as a CPU or other processor reading and executing a software program from a recording medium such as a hard disk or a semiconductor memory.

It is also contemplated that the implementation of the components of the present disclosure can be done with any newly arising technology that may replace any of the above implementation technologies.

The system of the present disclosure is a modular system providing a universal and scalable platform including a monitor mount capable of mixed use with monitors having different sizes. Traditionally, each type of patient monitor typically required a dedicated monitor mount, a dedicated controller, and a dedicated user interface. Accordingly, traditional monitors of different sizes are not interoperable and the performance advantages of each type of monitor cannot be combined and leveraged. However, since the system of the present disclosure enables the mounting of two monitors having different sizes, shapes, and functionality on a single monitor mount, the two monitors are interoperable with the same controller and the same user interface, and can be universally docked to the monitor mount.

What is claimed is:

1. A system comprising:
   a monitor mount including a support portion;
   a first monitor including a first electronic visual display, the first monitor having a first monitor width in a lateral direction of the first monitor; and
   a second monitor including: (i) a second electronic visual display; and (ii) a receptacle including a bridge portion and a coupling, the bridge portion having a bridge width in a lateral direction of the second monitor, the second monitor having a second monitor width in a lateral direction of the second monitor, the receptacle further comprising a guiding surface configured to receive the first monitor to be inserted into the receptacle in a first position and rotate the first monitor into a secured position within the second monitor, the first monitor being engaged with the coupling in the secured position;

wherein:

the second monitor is configured to be detachably secured to the monitor mount by the support portion;

the first monitor is configured to be detachably secured to the second monitor by the coupling such that the first monitor is received in the receptacle of the second monitor and the bridge portion of the second monitor extends over the first monitor;

the second monitor is configured to surround at least a portion of the first electronic visual display of the first monitor when the first monitor is detachably secured to the second monitor; and the bridge width being less than the second monitor width and being less than the first monitor width.

2. The system of claim 1, wherein the receptacle and the bridge width are adapted to enable the first monitor to be inserted into the receptacle in a direction that is non-parallel to a floor of the receptacle, then rotated into a secured position within the second monitor, the first monitor being engaged with the coupling and parallel to the floor of the receptacle in the secured position.

3. The system of claim 1, wherein the second monitor further comprises a guiding surface that is distal to the bridge.

4. The system of claim 1, wherein the second monitor includes a back portion having back portion width in the lateral direction of the second monitor and the bridge width is less than the second back portion width.

5. The system of claim 4, wherein the bridge width is no more than half of the second back portion width.

6. The system of claim 1, wherein the bridge width is sufficiently small relative to the second monitor width so as to define at least one upwardly facing opening.

7. A monitor comprising:

an electronic visual display; and a receptacle including a bridge portion and a coupling, the bridge portion having a bridge width in a lateral direction of the monitor;

wherein:

the coupling is configured to detachably secure another monitor such that the other monitor is received in the receptacle of the monitor and the bridge portion of the monitor extends over the other monitor; and the monitor is configured to surround at least a portion of an electronic visual display of the other monitor when the other monitor is detachably secured to the monitor; and the bridge width being less than a width of the monitor in the lateral direction of the monitor and being less than a width of the other monitor in a lateral direction of the other monitor.

8. The monitor of claim 7, wherein:

the receptacle of the second monitor includes two parallel surfaces; and the receptacle of the second monitor is configured to receive the first monitor such that the first monitor is adjacent to the bridge portion of the second monitor, the two parallel surfaces of the second monitor, and the coupling of the second monitor.

9. The monitor of claim 7, wherein the coupling includes at least one guiding surface configured to initially receive the first monitor and thereafter guide the first monitor to a secured position within the second monitor.

10. The monitor of claim 7, wherein the coupling includes at least one guiding surface configured to initially receive the first monitor at an angle such that the first monitor is rotated and thereafter guide the first monitor to a secured position within the second monitor.

11. The monitor of claim 7, wherein the bridge portion of the second monitor includes a lateral slot and a top portion of the first monitor is configured to be transversely inserted into the lateral slot.

12. The monitor of claim 7, wherein the second monitor includes a handle.

13. The monitor of claim 7, wherein bridge portion of the second monitor and the handle of the second monitor are formed as a single unit.

14. The monitor of claim 7, wherein a top portion of the second monitor includes holes for repositioning the bridge portion of the second monitor.

15. The monitor of claim 7, wherein the support portion is configured to support a bottom face of the second monitor.

16. The monitor of claim 7, wherein the support portion is configured to detachably secure a handle of the second monitor.

17. The monitor of claim 7, wherein the support portion is at least one of a shelf, a ledge, a rail, a rib and an abutment.

18. The monitor of claim 7, wherein the support portion includes a release mechanism for releasing the second monitor from the monitor mount.

19. The monitor of claim 7, wherein the monitor mount further comprises a power bus configured to power at least one of the first monitor and the second monitor when the at least one of the first monitor and the second monitor is secured to the monitor mount.

20. The monitor of claim 7, wherein the first monitor further comprises a sensor interface configured to receive data generated by a physiological sensor monitoring a physiological parameter of a patient.

21. The monitor of claim 7, wherein the second monitor further comprises a guiding surface that is distal to the bridge.

22. The monitor of claim 7, wherein the second monitor includes a back portion having back portion width in the lateral direction of the second monitor and the bridge width is less than the second back portion width.

23. The monitor of claim 22, wherein the bridge width is no more than half of the second back portion width.

24. The monitor of claim 7, wherein the bridge width is sufficiently small relative to the second monitor width so as to define at least one upwardly facing opening.

* * * * *